US012564316B2

(12) United States Patent
Hameed et al.

(10) Patent No.: US 12,564,316 B2
(45) Date of Patent: Mar. 3, 2026

(54) ENDOSCOPE WITH BENDABLE CAMERA SHAFT

(71) Applicant: PSIP2 LLC, Manchester, NH (US)

(72) Inventors: Salmaan Hameed, San Jose, CA (US);
Michael Herda, Boxford, MA (US);
Siddharth Desai, Mission Viejo, CA
(US)

(73) Assignee: PSIP2 LLC, Manchester, NH (US)

( * ) Notice: Subject to any disclaimer, the term of this
patent is extended or adjusted under 35
U.S.C. 154(b) by 0 days.

(21) Appl. No.: 17/361,711

(22) Filed: Jun. 29, 2021

(65) Prior Publication Data

US 2022/0007918 A1      Jan. 13, 2022

Related U.S. Application Data

(60) Provisional application No. 63/214,296, filed on Jun.
24, 2021, provisional application No. 63/067,781,
(Continued)

(51) Int. Cl.
A61B 1/06 (2006.01)
A61B 1/00 (2006.01)
(Continued)

(52) U.S. Cl.
CPC .......... A61B 1/008 (2013.01); A61B 1/00124
(2013.01); A61B 1/00128 (2013.01);
(Continued)

(58) Field of Classification Search
CPC . A61B 1/008; A61B 1/00124; A61B 1/00128;
A61B 1/00142; A61B 1/00165;
(Continued)

(56) References Cited

U.S. PATENT DOCUMENTS

| | | | |
|---|---|---|---|
| 4,121,206 A | 10/1978 | LeMire | |
| 4,273,110 A | 6/1981 | Groux | |
| (Continued) | | | |

FOREIGN PATENT DOCUMENTS

| | | | |
|---|---|---|---|
| CN | 2551172 Y | 5/2003 | |
| CN | 2868212 Y | 2/2007 | |
| (Continued) | | | |

OTHER PUBLICATIONS

Written Opinion of International Application No. PCT/IB2021/
055823, Dated May 16, 2022.
(Continued)

*Primary Examiner* — Michael J Carey
*Assistant Examiner* — Christen A. Sharpless
(74) *Attorney, Agent, or Firm* — BOND, SCHOENECK
& KING PLLC

(57) ABSTRACT

An endoscope with a handle and an insertion shaft. The
insertion shaft has solid state illumination and imaging
circuitry at or near a tip designed to provide illumination and
imaging of a body cavity for a surgeon during surgery. At
least a portion of the insertion shaft is flexible or articulated.
Controls on the handle permit control of flex or articulation
of the insertion shaft to permit direction of illumination and
field of view of the imaging circuitry. Control force transfer
elements permit a surgeon to direct a direction of the
imaging circuitry by transfer of mechanical force directed by
a surgeon to the bendable distal portion to cause the bend-
able portion to bend under the surgeon's control.

30 Claims, 23 Drawing Sheets

Related U.S. Application Data filed on Aug. 19, 2020, provisional application No. 63/047,588, filed on Jul. 2, 2020, provisional application No. 63/046,665, filed on Jun. 30, 2020.

(51) Int. Cl.
   *A61B 1/005*      (2006.01)
   *A61B 1/008*      (2006.01)

(52) U.S. Cl.
   CPC ...... *A61B 1/00142* (2013.01); *A61B 1/00165* (2013.01); *A61B 1/0057* (2013.01); *A61B 1/0676* (2013.01); *A61B 1/0684* (2013.01)

(58) Field of Classification Search
   CPC ... A61B 1/0057; A61B 1/0676; A61B 1/0684; A61B 1/00183; A61B 1/0052; A61B 1/05; A61B 1/07; A61B 1/122; A61B 1/123; A61B 1/00105
   See application file for complete search history.

(56) References Cited

U.S. PATENT DOCUMENTS

| | | | |
|---|---|---|---|
| 4,765,313 A | 8/1988 | Kumakura | |
| 4,852,551 A | 8/1989 | Opie | |
| 4,895,138 A | 1/1990 | Yabe | |
| 4,919,112 A | 4/1990 | Siegmund | |
| 4,964,710 A | 10/1990 | Leiner | |
| 4,997,084 A | 3/1991 | Opie | |
| 5,122,192 A | 6/1992 | Inukai et al. | |
| 5,165,387 A | 11/1992 | Woodson | |
| 5,188,092 A | 2/1993 | White | |
| 5,377,047 A | 12/1994 | Broome | |
| 5,398,685 A | 3/1995 | Wilk et al. | |
| 5,519,532 A | 5/1996 | Broome | |
| 5,573,493 A | 11/1996 | Sauer | |
| 5,653,677 A | 8/1997 | Okada | |
| 5,711,299 A | 1/1998 | Manwaring et al. | |
| 5,711,755 A | 1/1998 | Bonnell | |
| 5,718,664 A | 2/1998 | Peck | |
| 5,892,630 A | 4/1999 | Broome | |
| 6,203,493 B1 | 3/2001 | Ben-Haim | |
| 6,261,226 B1 | 7/2001 | McKenna et al. | |
| 6,293,910 B1 | 9/2001 | Yamakita | |
| 6,605,260 B1 | 8/2003 | Busted | |
| 6,611,700 B1 | 8/2003 | Vilsmeier et al. | |
| 6,652,452 B1 | 11/2003 | Seifert | |
| 6,865,825 B2 | 3/2005 | Bailey | |
| 6,928,314 B1 | 8/2005 | Johnson et al. | |
| 6,947,784 B2 | 9/2005 | Zalis | |
| 7,033,317 B2 | 4/2006 | Pruitt | |
| 7,239,805 B2 | 7/2007 | Uyttendaele | |
| 7,413,543 B2 | 8/2008 | Banik | |
| 7,427,262 B2 | 9/2008 | Bonningue | |
| 7,479,106 B2 | 1/2009 | Banik | |
| 7,530,946 B2 | 5/2009 | Hartwick | |
| 7,976,559 B2 | 7/2011 | Goldfarb | |
| 8,009,167 B2 | 8/2011 | Dekel et al. | |
| 8,075,478 B2 | 12/2011 | Campos | |
| 8,187,170 B2 | 5/2012 | Naito | |
| 8,257,386 B2 | 9/2012 | Lee | |
| 8,398,540 B2 | 3/2013 | Hassidov | |
| 8,449,456 B2 | 5/2013 | Ueno | |
| 8,556,806 B2 | 10/2013 | Farr | |
| 8,812,125 B2 | 8/2014 | Kaula et al. | |
| 8,827,899 B2 | 9/2014 | Farr | |
| 8,858,425 B2 | 10/2014 | Farr | |
| 9,066,658 B2 | 6/2015 | Hamel | |
| 9,107,574 B2 | 8/2015 | Goldfarb | |
| 9,116,282 B2 | 8/2015 | Kazakevich | |
| 9,242,069 B2 | 1/2016 | Alt | |
| 9,271,637 B2 | 3/2016 | Farr | |
| 9,364,249 B2 | 6/2016 | Kimball | |
| 9,504,373 B2 | 11/2016 | Vayser | |
| 9,877,654 B2 | 1/2018 | Tesar | |
| 9,895,048 B2 | 2/2018 | Ouyang | |
| 10,105,040 B2 | 10/2018 | Ochi | |
| 10,278,563 B2 | 5/2019 | Ouyang | |
| 10,780,187 B2 | 9/2020 | Kang | |
| 11,141,045 B2 | 10/2021 | Kucharski | |
| 11,147,636 B2 | 10/2021 | Hallen | |
| 11,185,216 B2 | 11/2021 | Heni | |
| 11,278,194 B2 | 3/2022 | Benning | |
| 11,357,064 B2 | 6/2022 | Pan et al. | |
| 11,357,593 B2 | 6/2022 | Komp | |
| 2001/0031115 A1 | 10/2001 | Chen | |
| 2002/0035330 A1 | 3/2002 | Cline et al. | |
| 2002/0077850 A1 | 6/2002 | McMenimen et al. | |
| 2003/0007672 A1 | 1/2003 | Harman et al. | |
| 2003/0158503 A1 | 8/2003 | Matsumoto | |
| 2003/0167007 A1 | 9/2003 | Belson | |
| 2004/0075848 A1 | 4/2004 | Baumann et al. | |
| 2004/0098040 A1 | 5/2004 | Taniguchi | |
| 2005/0234294 A1* | 10/2005 | Saadat | A61B 1/0008 |
| | | | 600/104 |
| 2006/0149127 A1 | 7/2006 | Seddiqui | |
| 2006/0276692 A1 | 12/2006 | Kucklick | |
| 2007/0015967 A1 | 1/2007 | Boulais et al. | |
| 2007/0049794 A1 | 3/2007 | Glassenberg et al. | |
| 2007/0103460 A1 | 5/2007 | Zhang et al. | |
| 2007/0183685 A1 | 8/2007 | Wada et al. | |
| 2007/0202005 A1 | 8/2007 | Maschke | |
| 2007/0225556 A1* | 9/2007 | Ortiz | A61B 1/0684 |
| | | | 600/172 |
| 2007/0249904 A1 | 10/2007 | Amano | |
| 2008/0027283 A1 | 1/2008 | Matsui | |
| 2008/0051802 A1 | 2/2008 | Schostek | |
| 2008/0199829 A1 | 8/2008 | Paley et al. | |
| 2008/0247375 A1 | 10/2008 | Muharemovic et al. | |
| 2008/0285309 A1 | 11/2008 | Fang et al. | |
| 2008/0300456 A1 | 12/2008 | Irion | |
| 2009/0055215 A1 | 2/2009 | Giraldo et al. | |
| 2009/0076329 A1 | 3/2009 | Su | |
| 2009/0082630 A1 | 3/2009 | Tulley | |
| 2009/0128136 A1 | 5/2009 | Hablizel | |
| 2009/0299363 A1* | 12/2009 | Saadat | A61B 1/0008 |
| | | | 606/41 |
| 2010/0042439 A1 | 2/2010 | Martinez et al. | |
| 2010/0138238 A1 | 6/2010 | Sobie | |
| 2010/0198009 A1 | 8/2010 | Farr | |
| 2010/0204546 A1 | 8/2010 | Hassidov | |
| 2010/0261961 A1 | 10/2010 | Scott et al. | |
| 2011/0009694 A1* | 1/2011 | Schultz | A61B 10/0233 |
| | | | 600/109 |
| 2011/0028790 A1 | 2/2011 | Farr | |
| 2011/0096570 A1 | 4/2011 | Vissenberg et al. | |
| 2011/0237880 A1 | 9/2011 | Hamel | |
| 2012/0029280 A1 | 2/2012 | Kucklick | |
| 2012/0116398 A1* | 5/2012 | Goldfarb | A61B 46/17 |
| | | | 606/49 |
| 2012/0197078 A1 | 8/2012 | Stanley | |
| 2013/0012773 A1 | 1/2013 | Kwan | |
| 2013/0012783 A1 | 1/2013 | Vayser | |
| 2013/0204083 A1 | 8/2013 | Schmieding et al. | |
| 2013/0253499 A1 | 9/2013 | Kimball | |
| 2013/0299844 A1 | 11/2013 | Zhao | |
| 2013/0324973 A1* | 12/2013 | Reed | A61M 25/0097 |
| | | | 604/528 |
| 2014/0061304 A1 | 3/2014 | Drees et al. | |
| 2014/0067406 A1 | 3/2014 | Hyatt et al. | |
| 2014/0107416 A1* | 4/2014 | Birnkrant | A61B 1/00105 |
| | | | 600/110 |
| 2014/0114129 A1* | 4/2014 | Peh | A61B 1/008 |
| | | | 600/141 |
| 2014/0125482 A1 | 5/2014 | Rigsby et al. | |
| 2014/0221749 A1 | 8/2014 | Grant | |
| 2014/0243592 A1* | 8/2014 | Kato | A61B 17/00234 |
| | | | 600/141 |
| 2014/0275771 A1 | 9/2014 | Henley | |
| 2015/0011830 A1 | 1/2015 | Hunter | |
| 2015/0025311 A1 | 1/2015 | Kadan | |
| 2015/0069728 A1 | 3/2015 | Seitz, III | |

(56) References Cited

U.S. PATENT DOCUMENTS

| | | | |
|---|---|---|---|
| 2015/0164305 A1* | 6/2015 | Kohno | A61B 1/00042 |
| | | | 600/149 |
| 2015/0164313 A1 | 6/2015 | Ouyang | |
| 2015/0173594 A1 | 6/2015 | Farhadi | |
| 2015/0327886 A1 | 11/2015 | Shen | |
| 2015/0374210 A1 | 12/2015 | Durr | |
| 2016/0015467 A1 | 1/2016 | Vayser et al. | |
| 2016/0030962 A1 | 2/2016 | Sinnott et al. | |
| 2016/0085922 A1 | 3/2016 | Sweeney | |
| 2016/0235286 A1 | 8/2016 | Chiang | |
| 2016/0283900 A1 | 9/2016 | Johnson et al. | |
| 2017/0035277 A1 | 2/2017 | Kucharski et al. | |
| 2017/0049298 A1* | 2/2017 | Hunter | A61B 5/067 |
| 2017/0066000 A1 | 3/2017 | Schwab et al. | |
| 2017/0070654 A1 | 3/2017 | Ochi | |
| 2017/0078583 A1* | 3/2017 | Haggerty | A61B 1/00071 |
| 2017/0182194 A1 | 6/2017 | Shin | |
| 2017/0185953 A1 | 6/2017 | Daliforno et al. | |
| 2017/0188795 A1 | 7/2017 | Ouyang | |
| 2017/0202005 A1 | 7/2017 | Madan et al. | |
| 2017/0245890 A1 | 8/2017 | Ochi | |
| 2018/0084986 A1 | 3/2018 | Ochi | |
| 2018/0160003 A1 | 6/2018 | Sutoh et al. | |
| 2018/0168442 A1 | 6/2018 | Schaeffer | |
| 2018/0235441 A1 | 8/2018 | Huang | |
| 2018/0296281 A1 | 10/2018 | Yeung et al. | |
| 2018/0317762 A1* | 11/2018 | Fowler | A61B 1/00098 |
| 2019/0038116 A1 | 2/2019 | Ochi | |
| 2019/0136070 A1 | 5/2019 | Aizenberg et al. | |
| 2019/0150711 A1 | 5/2019 | Chiu et al. | |
| 2019/0206281 A1 | 7/2019 | Dantes et al. | |
| 2019/0298151 A1 | 10/2019 | Frangioni | |
| 2019/0328217 A1 | 10/2019 | Moreau | |
| 2019/0364492 A1 | 11/2019 | Azizi et al. | |
| 2019/0374095 A1 | 12/2019 | Lord | |
| 2020/0000491 A1 | 1/2020 | Washburn | |
| 2020/0105404 A1 | 4/2020 | Major et al. | |
| 2020/0174174 A1 | 6/2020 | Honda | |
| 2020/0205209 A1 | 6/2020 | Pan et al. | |
| 2020/0222146 A1 | 7/2020 | Komp | |
| 2020/0229205 A1 | 7/2020 | Bharadwaj et al. | |
| 2020/0329953 A1 | 10/2020 | Truckai | |
| 2020/0345218 A1 | 11/2020 | Lord | |
| 2020/0397232 A1 | 12/2020 | Ulmschneider | |
| 2021/0052145 A1* | 2/2021 | Rauniyar | A61B 1/00096 |
| 2021/0113068 A1* | 4/2021 | Shin | A61B 1/0055 |
| 2021/0169316 A1 | 6/2021 | Schultheis | |
| 2021/0220014 A1 | 7/2021 | Gitelis | |
| 2021/0330177 A1 | 10/2021 | Kohno | |
| 2021/0337455 A1 | 10/2021 | Zhou et al. | |
| 2021/0407662 A1 | 12/2021 | Souffrou | |
| 2022/0020480 A1 | 1/2022 | Monaghan et al. | |
| 2022/0030519 A1 | 1/2022 | Zhou et al. | |
| 2022/0046166 A1 | 2/2022 | Holmstrom | |
| 2022/0125280 A1 | 4/2022 | Tyan | |
| 2022/0174690 A1 | 6/2022 | Wang et al. | |
| 2022/0254482 A1 | 8/2022 | Souffrou | |
| 2022/0264677 A1 | 8/2022 | Pan et al. | |
| 2022/0378279 A1 | 12/2022 | Poll | |
| 2023/0070386 A1 | 3/2023 | Koubi | |
| 2023/0123867 A1 | 4/2023 | Herda et al. | |
| 2023/0124488 A1 | 4/2023 | Noyes et al. | |
| 2023/0146057 A1 | 5/2023 | Moore et al. | |
| 2024/0355465 A1 | 10/2024 | Amos et al. | |

FOREIGN PATENT DOCUMENTS

| | | |
|---|---|---|
| CN | 101040775 | 9/2007 |
| CN | 101801278 | 8/2010 |
| CN | 103315807 | 9/2013 |
| CN | 106308727 | 1/2017 |
| CN | 106821285 | 6/2017 |
| CN | 107 157 429 | 9/2017 |
| CN | 111458859 A | 7/2020 |
| CN | 115868909 A | 3/2023 |
| CN | 116250798 A | 6/2023 |
| DE | 10330177 A1 | 3/2005 |
| DE | 102018131380 A1 | 6/2020 |
| EP | 1634656 A1 | 3/2006 |
| EP | 1902665 | 3/2008 |
| EP | 2266452 | 12/2010 |
| EP | 2266452 A2 | 12/2010 |
| EP | 3675533 A1 | 7/2020 |
| GB | 2300717 A | 11/1996 |
| JP | H09285748 A | 11/1997 |
| JP | 2001-128923 A | 5/2001 |
| JP | 2002-512086 | 4/2002 |
| JP | 2003-10742 A | 1/2003 |
| JP | 2004-358107 | 12/2004 |
| JP | 2007-20797 | 2/2007 |
| JP | 2008092440 A | 4/2008 |
| JP | 4315489 B2 | 8/2009 |
| JP | 2009172202 A | 8/2009 |
| JP | 2010137166 A | 6/2010 |
| JP | 2014-066923 A | 4/2014 |
| JP | 2013-192953 | 9/2018 |
| KR | 10-1614939 | 4/2016 |
| KR | 20160044635 A | 4/2016 |
| KR | 10-1784213 | 10/2017 |
| KR | 102123112 B1 | 6/2020 |
| WO | WO 1993/015648 A2 | 8/1993 |
| WO | 0904725 B1 | 9/2005 |
| WO | WO 2006/073676 A1 | 7/2006 |
| WO | 2008136283 A1 | 11/2008 |
| WO | WO 2012/027581 A2 | 3/2012 |
| WO | WO 2014/031192 A1 | 2/2014 |
| WO | WO 2015/142720 A1 | 9/2015 |
| WO | WO 2017/040692 A1 | 3/2017 |
| WO | WO 2017/147605 | 8/2017 |
| WO | WO 2019/234712 | 12/2019 |
| WO | 2021087134 A1 | 5/2021 |
| WO | WO 2021/144778 | 7/2021 |
| WO | 2021163527 A1 | 8/2021 |
| WO | WO 2021/161228 | 8/2021 |
| WO | 2022020298 A1 | 1/2022 |
| WO | WO2022/003569 | 1/2022 |
| WO | WO 2023/026257 | 3/2023 |
| WO | WO 2023/053042 | 4/2023 |

OTHER PUBLICATIONS

PCT/IB2021/055823, International Search Report and Written Opinon (Aug. 10, 2021).
PCT/IB2021/055823, International Search Report and Written Opinion (Aug. 10, 2021).
PCT/IB2021/055823, Article 34 Amendment (Mar. 30, 2022).
PCT/IB2021/055823, Written Opinion (May 16, 2022).
PCT/IB2019/054783, ISA/210 International Search Report and ISA/237 Written Opinion of the International Searching Authority (Oct. 24, 2019).
PCT/IB2021/050359, ISA/210 International Search Report, and ISA/237 Written Opinion of the International Searching Authority (May 18, 2021).
PCT/IB2021/050359, Article 34 Amendment (excerpts) (Nov. 18, 2021).
PCT/IB2021/050359, International Preliminary Report on Patentabilty (Chapter II) (Mar. 4, 2022).
PCT/IB2022/058030, ISA/210 Search Report and ISA/237 Written Opinion of the International Searching Authority (Dec. 19, 2022).
PCT/IB2022/058030, Article 34 Amendment (Mar. 19, 2023).
PCT/IB2022/059262, ISA/210 International Search Report and ISA/237 Written Opinion of the International Searching Authority (Dec. 14, 2022).
CN App. CN 201980038145.1 , Office Action with Search Report (Jun. 23, 2022).
CN App. CN 201980038145.1 , Reply to Office Action (Nov. 8, 2022).
CN App. CN 201980038145.1 , Office Action (Nov. 17, 2022).
EPO App. EP 19746152.8 , Communication pursuant to Article 94(3) EPC (Sep. 28, 2021).

(56) References Cited

OTHER PUBLICATIONS

EPO App. EP 19746152.8 , Reply to Communication pursuant to Article 94(3) (Feb. 7, 2022) EPO App. EP 19746152.8 , Extended European Search Report (Dec. 21, 2022).

EPO App. EP 197461528 , Extended European Search Report (Dec. 21, 2022).

EPO App. EP 19746152.8 , Communication pursuant to Article 94(3) EPC (Mar. 17, 2023).

Eduardo Martín Arranz, María Dolores Martín Arranz, Tomás Robredo, Pablo Mancheño-Corvo, Ramón Menta, Francisco Javier Alves, Jose Manuel Suárez de Parga, Pedro Mora Sanz, Olga de la Rosa, Dirk Büscher, Eleuterio Lombardo, and Fernando de Miguel: Endoscopic submucosal injection of adipose-derived mesenchymal stem cells ameliorates TNBS-induced colitis in rats and prevents stenosis, Stem Cell Research & Therapy 9:95, doi: 10.1186/s13287-018-0837-x (Apr. 10, 2018).

Felix Asche, Basler AG, White Paper, Modern CMOS Sensors and Their Use in Fluorescence-Based Applications (Nov. 2017).

Martin J. Hoogduijn, Eleuterio Lombardo, Concise Review: Mesenchymal Stromal Cells Anno 2019: Dawn of the Therapeutic Era? Stem Cells Translational Medicine 00:1-9 doi: 10.1002/sctm. 19-0073 (2019).

Oksana Kehoe, Alison Cartwright, Ayman Askari, Alicia J El Haj, and Jim Middleton: Intra-articular injection of mesenchymal stem cells leads to reduced inflammation and cartilage damage in murine antigen-induced arthritis, Journal of Translational Medicine 12:157, doi: 10.1186/1479- 5876-12-157 (Jun. 3, 2014).

Matthew J. Kraeutler, Tigran Garabekyan, Omer Mei-Dan, The use of platelet-rich plasma to augment conservative and surgical treatment of hip and pelvic disorders, Muscles, Ligaments and Tendons Journal 410 2016;6 (3):409-419 doi: 10.11138/mltj/2016.6.3.410 (Dec. 21, 2016).

Benedetta Mazzanti, Bruno Lorenzi, Annalisa Borghini, Margherita Boieri, Lara Ballerini, Riccardo Saccardi, Elisabetta Weber, and Federica Pessina: Local injection of bone marrow progenitor cells for the treatment of anal sphincter injury: in-vitro expanded versus minimally-manipulated cells, Stem Cell Research & Therapy 7:85, doi 10.1186/s13287-016-0344-x (Jun. 21, 2016).

Raffy Mirzayan, Joseph D. Cooper, and Jorge Chahla, Carbon Dioxide Insufflation of the Knee in the Treatment of Full-Thickness Chondral Defects With Micronized Human Articular Cartilage, Arthroscopy Techniques, 7:10:e969-e973, doi: 10.1016/j.eats.2018. 05.005 (Oct. 2018).

NanoSurgery Technology Corp., Product Technology, Introducing the NanoScope, http://nanosurgerytech.com/product-technology/ (accessed Sep. 15, 2019).

Trice Medical, Mi-eye 2 is the revolutionary alternative to a traditional MRI, https://tricemedical.com/mi-eye/ (accessed Jul. 25, 2019).

René von Fintel, Basler AG, White Paper, Modern CMOS Cameras as Replacements for CCD Cameras (May 2018).

PCT App. PCT/IB2022/054938, International Search Report and Written Opinion of the International Searching Authority (Nov. 29, 2022).

Adaptive Surface Technologies, Inc., AST has brought two distinct product groups to market, https://adaptivesurface.tech (retrieved May 21, 2021.

Harvard University, Hansjörg Wyss Institute for Biologically Inspired Engineering at Harvard University, *TLP: A Non-Stick Coating for Medical Devices*, https://wyss.harvard.edu/technology/tlp-a-non-stick-coating-for-medical-devices (retrieved May 21, 2021).

Steffi Sunny, George Cheng, Daniel Daniel, Peter Lo, Sebastian Ochoa, Caitlin Howell, Nicolas Vogel, Adnan Majid, Joanna Aizenberg, *Transparent antifouling material for improved operative field visibility in endoscopy*, Proceedings of the National Academy of Sciences U.S.A., Oct. 18, 2016;113(42):11676-11681. doi: 10.1073/pnas.1605272113 (Sep. 29, 2016).

PCT/IB2021/055823, International Preliminary Report on Patentability (Aug. 10, 2022).

PCT/IB2022/058030, International Preliminary Report on Patentability (Dec. 24, 2023).

PCT/IB2023/059287, ISA/210 International Search Report and ISA/237 Written Opinion of the International Searching Authority (Dec. 28, 2023).

Canada App. 3,102,585, Examination Report (Oct. 6, 2023).

Canada App. 3,165,314, Examination Report (Oct. 18, 2023).

China App. CN 201980038145.1, Office Action (Feb. 14, 2023).

EPO App. EP 19746152.8, Communication pursuant to Article 94(3) EPC (Nov. 14, 2023).

EPO App. 21741290.7, Extended European Search Report (Dec. 18, 2023).

Japan App. 2020-567600, Office Action (Mar. 7, 2023).

Japan App. 2020-567600, Office Action (Aug. 15, 2023).

Japan App. 2020-567600, Office Action (Nov. 28, 2023).

G. Nardini, G. Stea, A. Virdis, D. Sabella and M. Caretti, "Broadcasting in LTE-Advanced networks using multihop D2D communications," 2016 IEEE 27th Annual International Symposium on Personal, Indoor, and Mobile Radio Communications ( PIMRC), 2016, pp. 1-6, doi: 10.1109/PIMRC.2016.7794788. (Year: 2016).

Pizzi S, Rinaldi F, Molinaro A, Iera A, Araniti G. Energy-Efficient Multicast Service Delivery Exploiting Single FrequencyDevice-To-Device Communications in 5G New Radio Systems. Sensors (Basel). Jul. 9, 2018;18(7):2205. doi: 10.3390/s18072205. PMID: 29987221; PMCID: PMC6068625. (Year: 2018).

Arash Asadi et al: "WiFi Direct and LTE D2D in action" 2013 Ifip Wireless Days (WD), Nov. 1, 2013 (Nov. 1, 2013), pp. 1-8, XP055186549, DOI: 10.1109/WD.2013.6686520 ISBN: 978-1-47-990543-0 the whole document.

Kar Udit Narayana et al: "An overview of device-to-device communication in cellular networks", ICT Express, vol. 4, No. 4, Dec. 1, 2018 (Dec. 1, 2018), pp. 203-208, XP055831642, ISSN: 2405-9595, DOI: 10.1016/j.icte.2017.08.002 Retrieved from the Internet: URL:https://www.sciencedirect.com/science/article/pii/S2405959517301467/pdfft? md5=c15bc95c88dd22da76fef3066d80f3a9&pid=1-s2.0- S2405959517301467-main.pdf.

* cited by examiner

140

ENDOSCOPE WITH BENDABLE CAMERA SHAFT

BACKGROUND

This application is a non-provisional of U.S. Prov. App. Ser. No. 63/214,296, filed Jun. 24, 2021, titled "Endoscope with Bendable Camera Shaft," a non-provisional of U.S. Provisional App. Ser. No. 63/067,781, filed Aug. 19, 2020, titled "Endoscope with Articulated Camera Shaft," a non-provisional of U.S. Provisional Application Ser. No. 63/047,588, filed Jul. 2, 2020, titled "Endoscope with Articulated Camera Shaft," and a non-provisional of U.S. Provisional App. Ser. No. 63/046,665, filed Jun. 30, 2020, titled "Endoscope with Articulated Camera Shaft." The entire disclosure of these applications are incorporated herein by reference This application relates to endoscopes, laparoscopes, arthroscopes, colonoscopes, and similar apparatus, instruments, implements, or processes specially adapted or intended to be used for evaluating, examining, measuring, monitoring, studying, or testing living or dead human and animal bodies for medical purposes.

SUMMARY

In general, in a first aspect, the invention features a replaceable endoscope tip for an endoscope, that includes the following. An insertion shaft has a rigid proximal portion and a distal portion, the distal portion being bendable to direct a field of view of imaging circuitry in a desired direction. Illuminator and solid state imaging circuitry are located at or near a distal tip of the articulable distal portion, the illuminator being designed to illuminate, and the imaging circuitry being designed to capture imaging of, an interior of a body cavity for a surgeon during surgery. A coupling is designed to separably connect the replaceable endoscope tip at a joint to a handle portion, and to disconnect the joint. The coupling has mechanical connectors designed: (a) when separated, the mechanical connectors permitting removal of the replaceable endoscope tip from the handle for disposal and replacement; and (b) when connected, the joint designed to provide mechanical force transfer between a surgeon's hand to the insertion shaft. Electrical connectors are designed to connect the replaceable endoscope tip to electronics in the handle, the handle electronics designed for drive of the illuminator and to receive imaging signal from the imaging circuitry, the handle being designed to permit sterilization between uses. Control force transfer elements are designed to permit a surgeon to direct a direction of the imaging circuitry by transfer of mechanical force directed by a surgeon to the bendable distal portion.

Embodiments of the invention may include one or more of the following features. These features may be used singly, or in combination with each other. The distal bendable portion may include a series of articulated rigid segments. A sheath or cover may cover the articulated rigid segments designed to reduce intrusion or pinching. The distal bendable portion may be formed of a solid component, bendable in its lateral and elevation dimensions, and relatively incompressible in compression in its longitudinal dimension. The distal bendable portion may be extendable from and retractable into a solid sheath. The distal bendable portion may be bendable in one dimension. The distal bendable portion may be bendable in two orthogonal dimensions. The imaging circuitry may be mounted within at or near a distal tip of the bendable distal portion via a pannable mounting. The pannable mounting may be designed as two sides of a parallelogram, and the imaging circuitry may be mounted on a structural segment hinged to the two parallelogram sides. Passages and apertures may be designed to pass irrigation fluid to improve view from a lens or window over the imaging circuitry. Passages and apertures may be designed to pass inflation fluid to enlarge a cavity for surgery. Mechanical connectors of the coupling may include a twist-lock designed to affix the endoscope replaceable endoscope tip to the handle portion. A plurality of the endoscope replaceable endoscope tips may be packaged for integrated shipment and sale with a reusable handle, the handle having electronics designed for drive of the illuminator and to receive imaging signal from the imaging circuitry. The illuminator may be an illumination LED mounted at or near the distal tip. The illuminator may be an emission end of a fiber optic fiber driven by an illumination source in the handle.

The above advantages and features are of representative embodiments only, and are presented only to assist in understanding the invention. It should be understood that they are not to be considered limitations on the invention as defined by the claims. Additional features and advantages of embodiments of the invention will become apparent in the following description, from the drawings, and from the claims.

DESCRIPTION

The Description is organized as follows.

I. Overview

II. Reposability: partially reusable, partially disposable/replaceable, and a coupling joint between III. Extendable, bendable, or articulated camera tip IV. Additional features of an endoscope V. Other embodiments

I. OVERVIEW

Figure 1A:
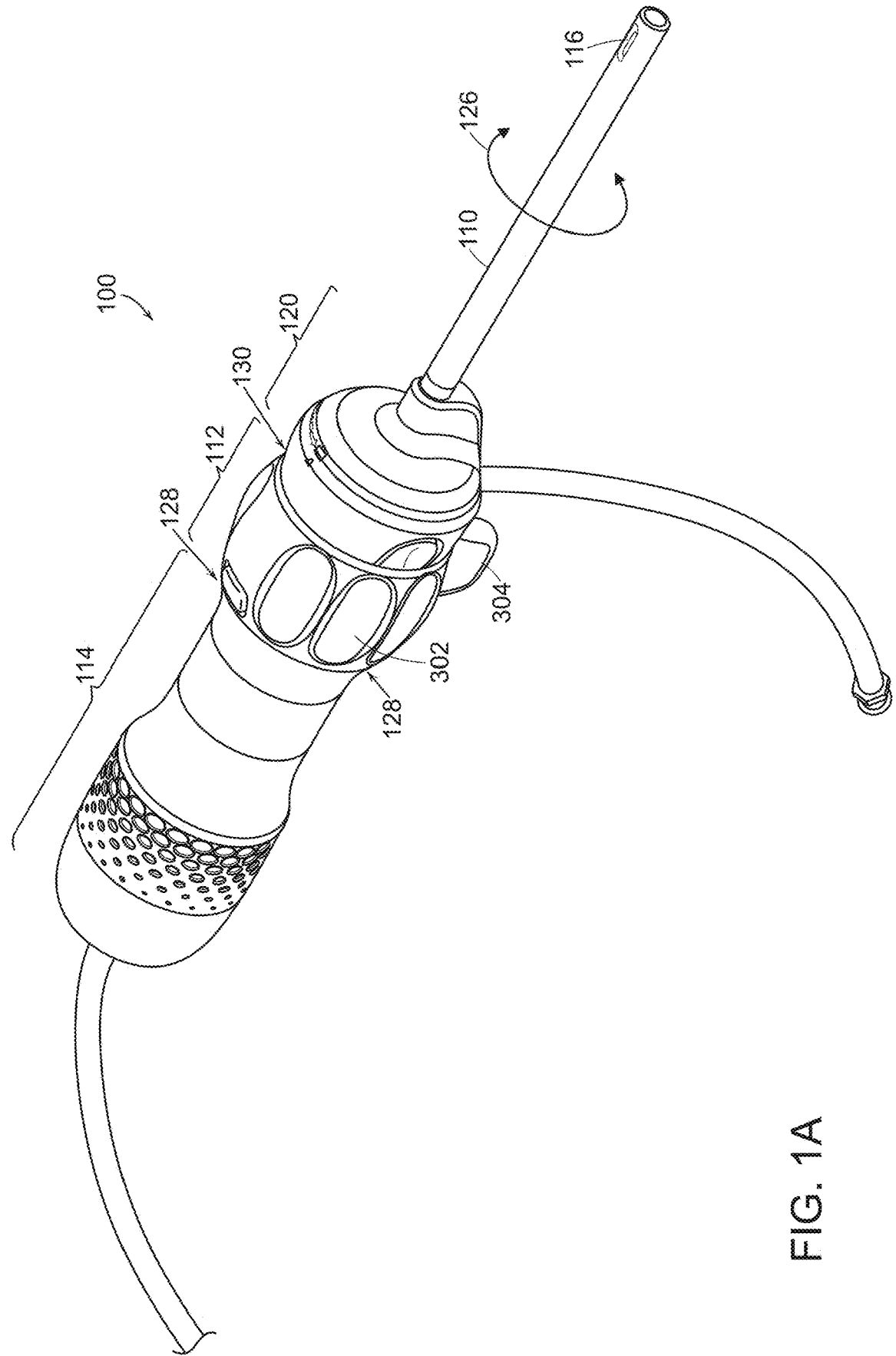
FIGS. 1A, 1C, 1D, 1E, 2A, 2B, 2C, 2I, 2K, 3A, 3E, 3G, 4A, and 5A are perspective views of endoscopes.
Figure 1B:
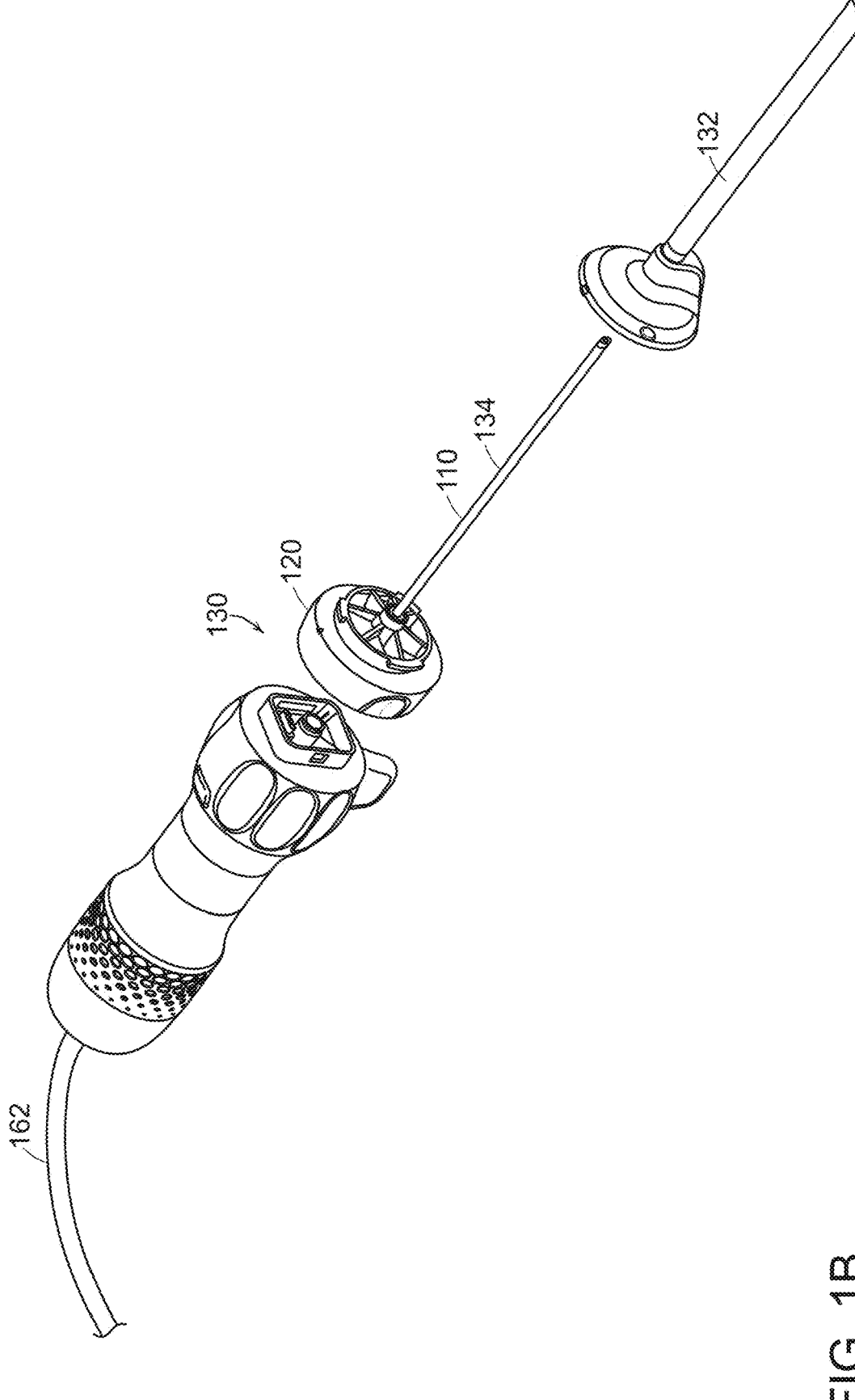
FIGS. 1B, 2D, 2J, 2L, 3B, 3C, 3D, 3F, 4B, 4C, 4D, and 5B show endoscopes, partially cut away.
Figure 1C:
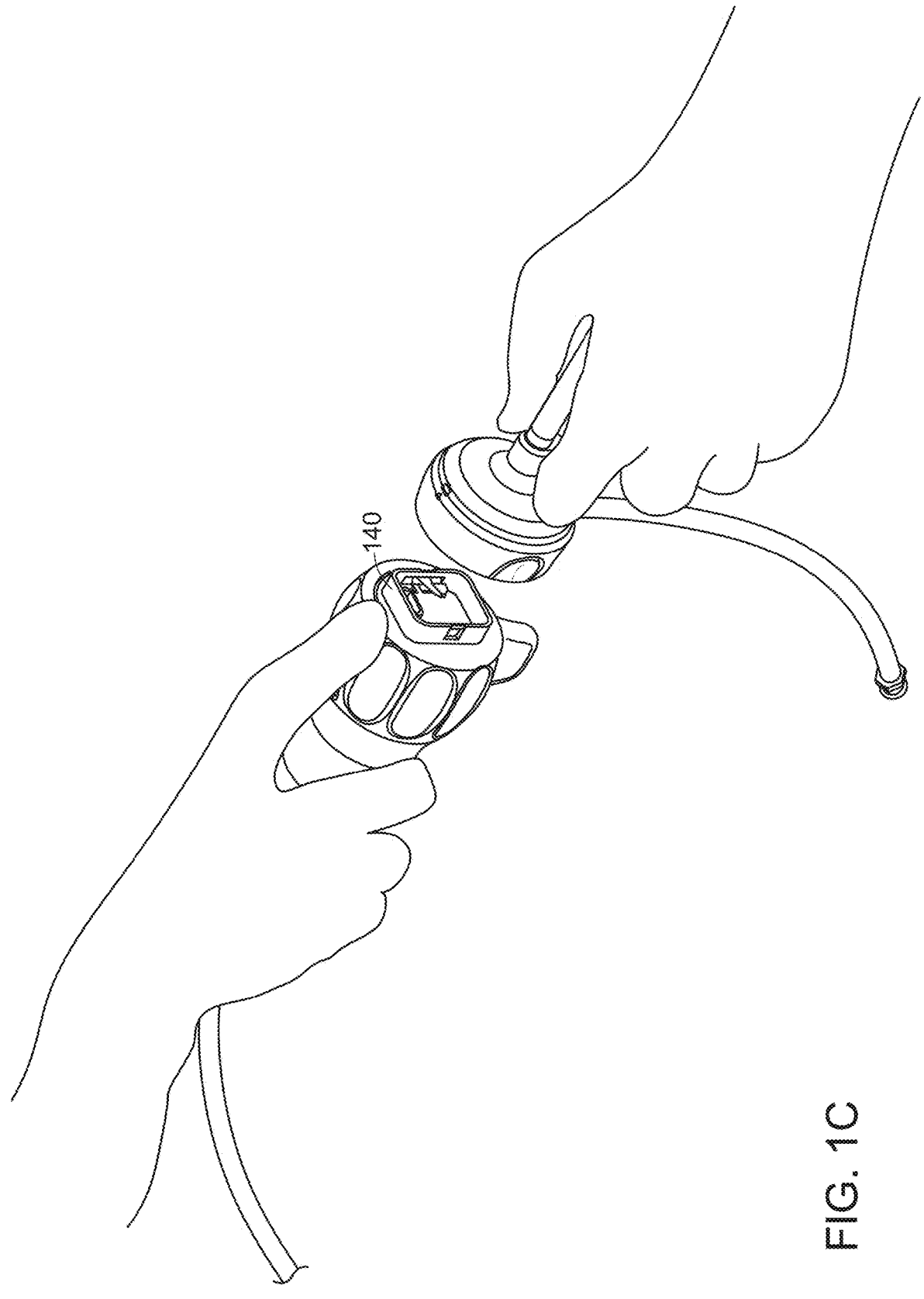

Referring to FIGS. 1A, 1B, and 1C, a surgical endoscope 100 may be structured to permit detachment of a shaft 110 portion from the endoscope's handle 112, 114. A camera or image sensor at tip 116 of the shaft, any panning mechanism, illumination, power and signal connectors, and fluid flow channels may be in the disposable shaft 110. Handle 112, 114 may be designed to be reusable (which implies that handle 112, 114 may be sterilizeable, for example in an autoclave or other sterilization device, or protectable by a disposable sterility sleeve). Joint 130 between the detachable shaft and the reusable parts of handle 112, 114 may be generally distal in the handle (but not necessarily at the distal-most end). The replaceable shaft portion 110 may be disposable, along with a disposable portion 120 of the handle that is disposable with shaft 110.

II. REPOSABILITY: PARTIALLY REUSABLE, PARTIALLY DISPOSABLE/REPLACEABLE, AND A COUPLING JOINT BETWEEN

Figure 3A:
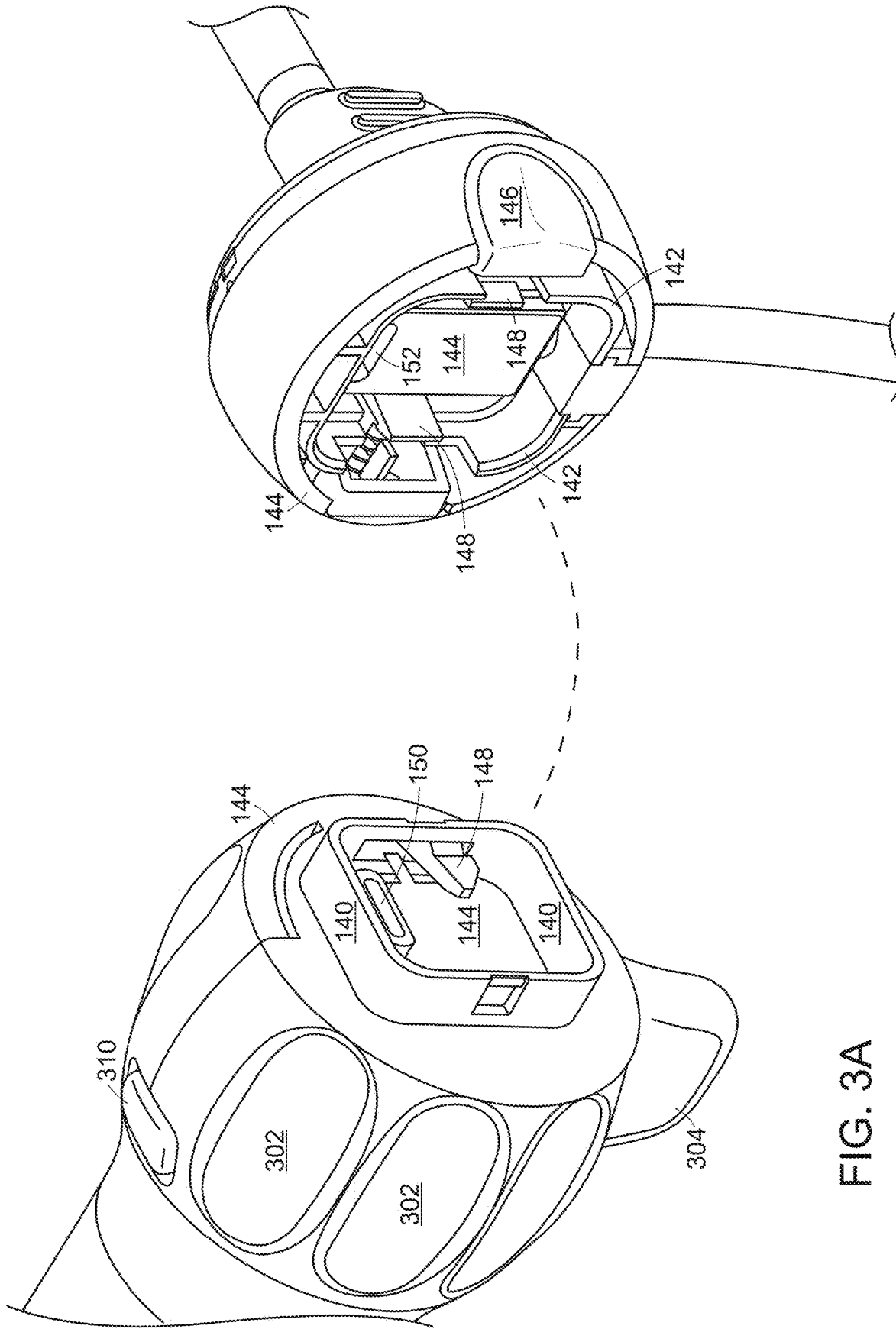
Figure 3B:
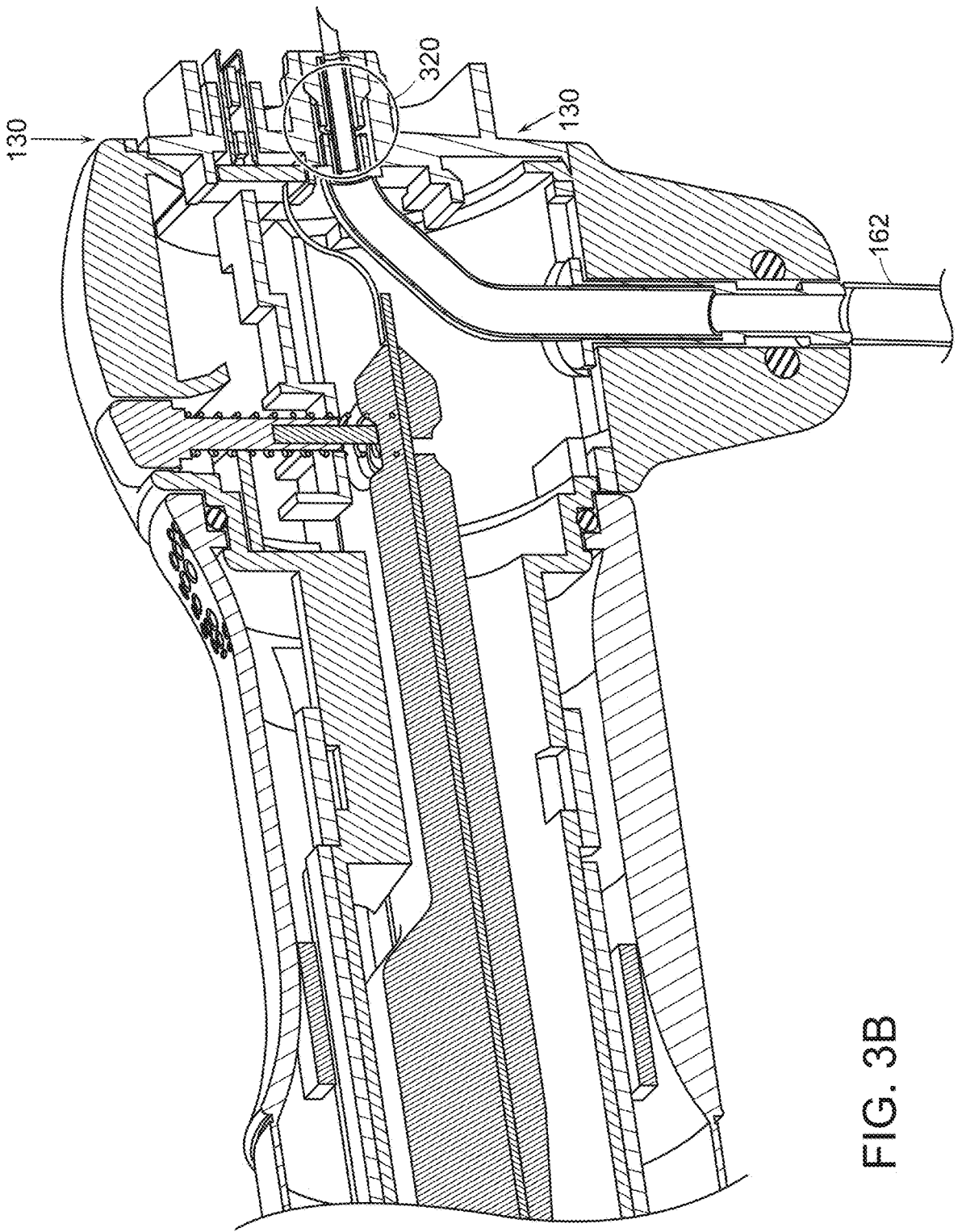

Referring to FIGS. 1A, 1C, and 3A, the handle of the endoscope 100 may include three principle components:

The disposable cap 120. This distal-most portion of the handle may serve as a mounting base for shaft 110, and may disconnect from the remainder 112, 114 of the handle. This disposable cap portion 120 (along with shaft 110 and componentry inside) may be disposable.

Rotation collar 112 may have surface features 302, 304 to allow a surgeon to rotate the rotation collar 120 about the central axis of the handle, that is, about the roll axis 126 of the shaft. During surgery, insertion shaft 110, disposable cap 120 and rotation collar 112 may be locked to rotate with each other, so that rotating the rotation collar effects rotation 126 of the disposable cap 120 and shaft 110.

Proximal stationary handle 114 has a shell surrounding componentry within the handle. The outer diameter and outer surface of handle 114 may be designed to provide an easy and low-slip grip for a surgeon's hand. Joint 128 between the proximal handle and rotation collar may allow these two components to rotate relative to each other. In some cases, a circuit board and similar componentry inside proximal handle 114 may rotate with disposable cap 120 and rotation collar 112, inside proximal handle 114.

Disposable cap 120 and rotation collar 112 may be separable from each other at joint 130, so that disposable cap 120 and shaft 110 may be disposable, while handle 114 and rotation collar 112 (and componentry inside them) are reusable.

Referring to FIGS. 1A, 1C, and 3A, between the disposable cap 120 and rotation collar 112, three basic connections may be made:

A rotation-locking coupling 140, 142 to hold the disposable portion 120 to the reusable handle 112, 114. Coupling 140, 142 may have sufficient strength to transmit insertion and withdrawal forces, roll, pitch, and yaw torques, lateral forces, and similar forces from the proximal reusable handle 112, 114 to the distal disposable portion 120 and shaft 100, thereby to allow a physician to aim the illumination and/or camera as needed. Joint 130 between disposable cap 120 and rotation collar 112 may lie generally toward the distal end of the handle. The disposable cap and rotation collar 112 may engage through flat force-transmittal surfaces 144 at the center of joint 130 and around the circumferences, so that these forces are supported around the circumference of separable joint 130. One or more release buttons 146 may be pressed or squeezed to cause one or more locking snaps 148 to disengage. The mechanical connection may include a rotatable locking ring or other release/fixation mechanisms.

An electrical connection to supply power to the illumination source and camera, and to carry optical signals back from the camera to the processing board in handle 112, 114 and display system outside the endoscope. The disconnectable electrical connections for power and signal may be effected by a USB-C connector 150, 152, mini HDMI connector, or similar connector that can maintain signal integrity for high speed signals. If illumination is conveyed by optical fiber, joint 130 may include an optical connector.

A disconnectable connection to any panning mechanism for the camera may be effected by a physical connector, such as a linkage.

In some cases, the camera/image sensor, LED, and electronic connections (and any mechanical connections for panning the camera/image sensor) may be removable from insertion shaft 110. Shaft 110 and cap 120 may be smooth and simple enough in shape to allow easy sterilization. Similarly, once the electronics are removed from interior of shaft 110, they may be sterilizeable as well. it may be cost-effective, especially in lower-labor-cost markets, to disassemble, sterilize, and reassemble the shaft and its interior components for reuse.

One or more fluid hoses 160 for irrigation liquid or inflation gas (or two hoses, one for fluid and one for gas) may enter through disposable cap 120, so that the entire set of fluid tubing for the irrigation/inflation channel may be disposable with the disposable shaft portion. In other cases (e.g., FIGS. 5(*a*) and 5(*b*)), a fluid hose 162 may enter the proximal end of the scope, and disconnectable fluid connections within joint 130 for fluid inflow and outflow may be effected by gaskets, O rings, and the like. Alternatively, connectors for the hoses may be outboard of the endoscope itself, either near the endoscope (for applications where it may be desirable to allow "quick change" replacement of the insertion shaft in the course of a single procedure), or far from the endoscope, typically at the receptacle for waste fluid, to ease disposal of all hoses that are potentially contaminated by contact with the patient.

Disposable shaft 110, 120 may be designed to facilitate disposability of components that come into contact with bodily fluids. Because sterilization is often imperfect, patient safety may be improved by disposing of components that have come into contact with patient bodily fluids. To improve sterilizability, it may desirable to reduce componentry in the disposable component 110, 120 so that cost of the disposable component may be reduced, and to reduce surface features and crevices that may be difficult to sterilize. Thus, the lens, image sensor, LED, panning mechanism, and shaft may be disposable. In addition, because shaft 110 is used for fluid inflow and outflow, and is disposable, sealing against bodily fluids may be unnecessary.

Figure 1D:
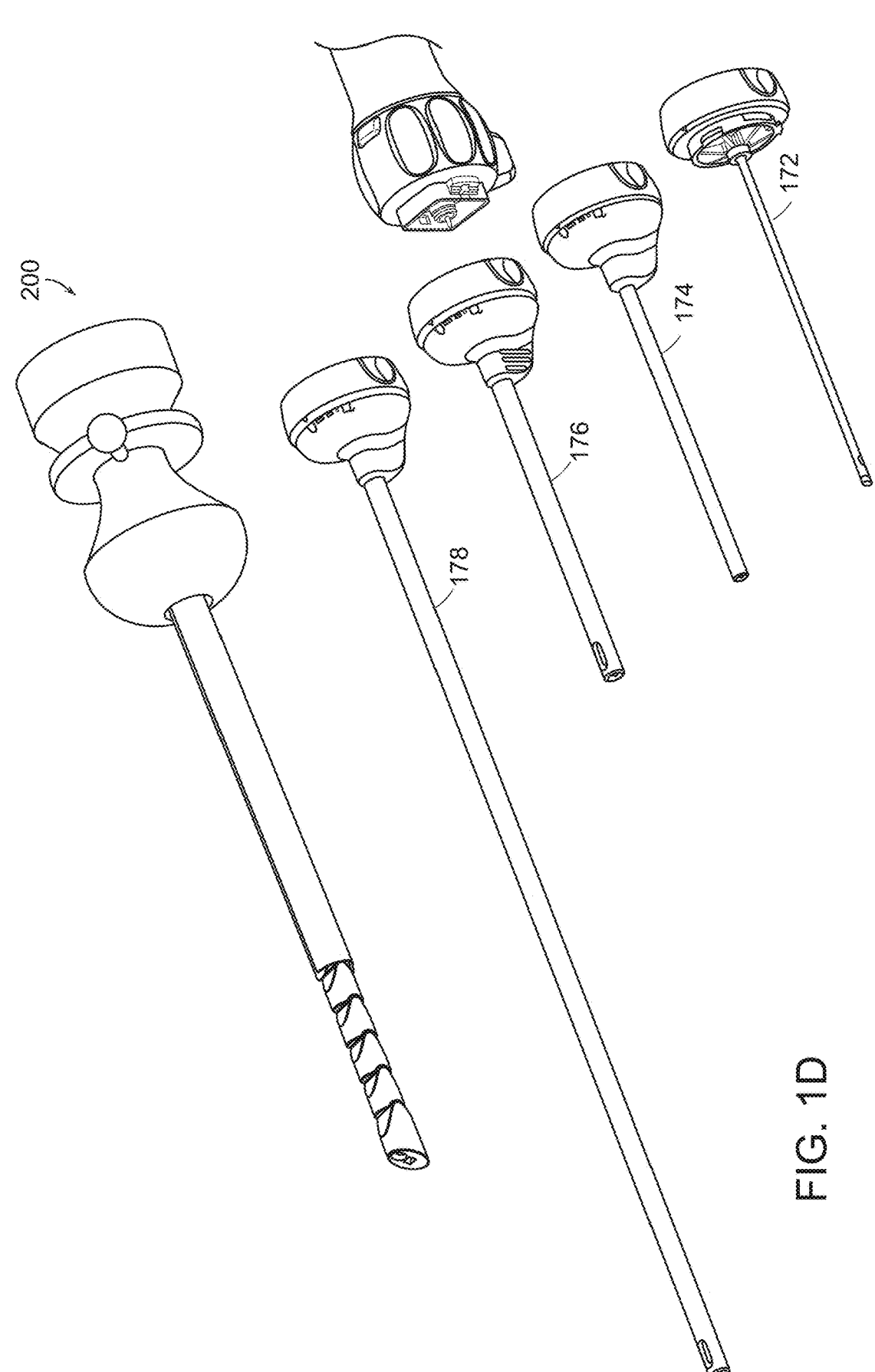

Referring to FIG. 1D, the replaceable/disposable shaft and its mounting componentry may be specialized to different types of surgery. For example, a purely diagnostic scope 172 may have an outer diameter of 1 to 3 mm. A replaceable disposable cap/shaft unit 110, 120, 178 for laparoscopic thoracic surgery may have a shaft of 400 mm length and diameter of 10 mm. Replaceable components 176 for arthroscopic surgery of knees and hips may be 155 mm in length, and 5.5 mm or 4 mm in diameter. For small joints, a replaceable shaft 174 of 2.9 mm diameter or less may be preferred. A replaceable shaft/scope unit with an bendable end 200 may be dimensioned for laparoscopic surgery. Typical dimensions for various surgical specialties may be as follows (measured in millimeters):

| Scope Type | Discipline | Cannula diameter | | Scope diameter | |
|---|---|---|---|---|---|
| | | Min | Max | Min | Max |
| Arthroscope (small joint) | Arthroscopy | 2.8 | 4.0 | 1.9 | 2.9 |
| Arthroscope (large joint) | Arthroscopy | 4.7 | 6.0 | 2.9 | 5.3 |

-continued

| | | Cannula diameter | | Scope diameter | |
| --- | --- | --- | --- | --- | --- |
| Scope Type | Discipline | Min | Max | Min | Max |
| Cytoscope | Cytoscopy | | | 2.9 | 5.3 |
| Encephaloscope | ENT | | | 2.0 | 4.0 |
| Hysteroscope | Gynecology | 3.7 | 7.0 | 2.0 | 5.0 |
| Laparoscope | Laparoscopy | | | 2.0 | 10.0 |
| Sinuscope | ENT | | | 2.0 | 4.0 |
| Thoracoscope | Pulmonary | | | | 10 |

Various replaceable components 110 may have different instruments at tip 116. For example, various replaceable shafts may have cameras oriented at 0° (directly on-axis), 30°, 45°, 70°, and 90°.

Figure 1E:
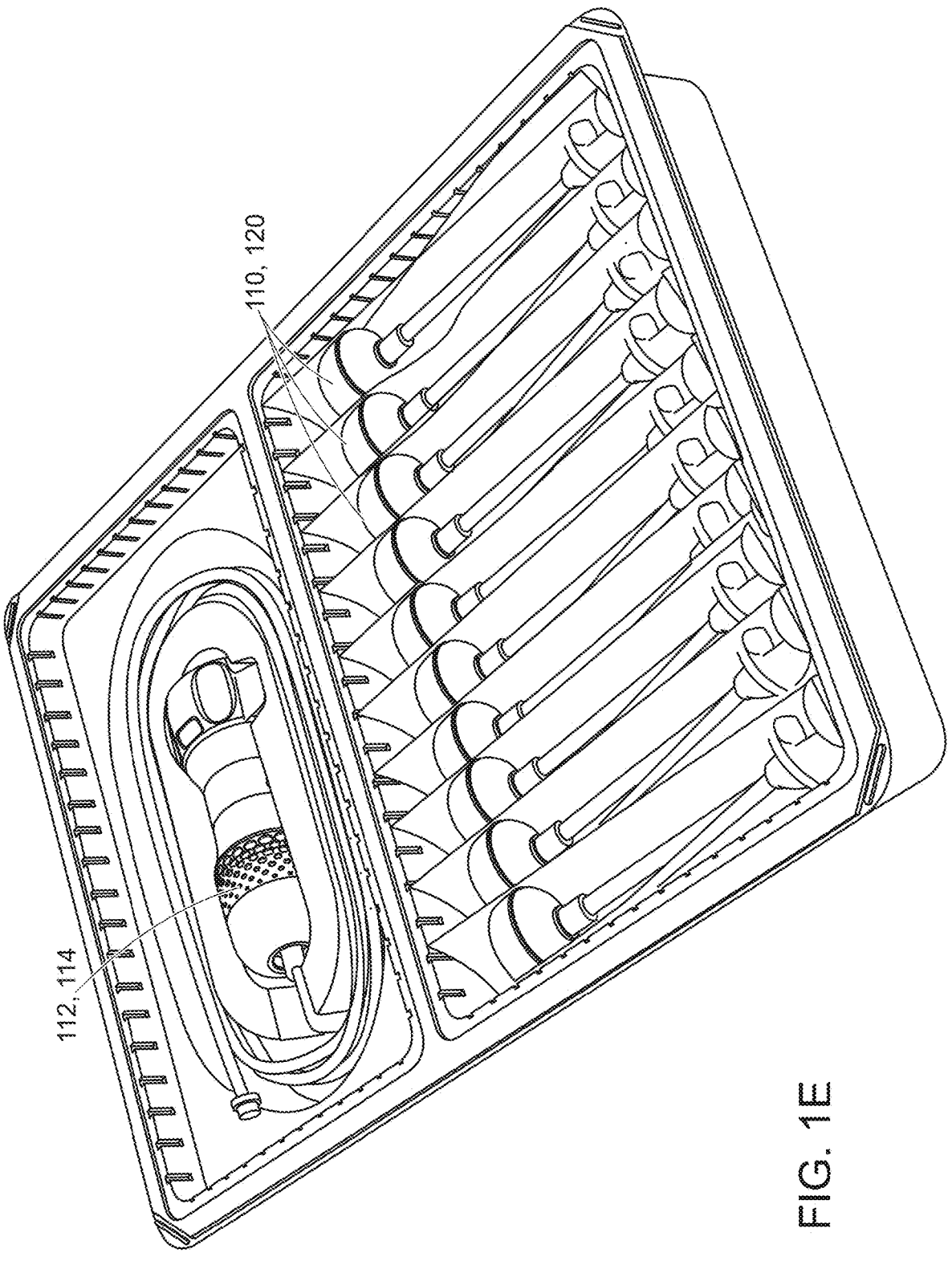

Referring to FIG. 1E, the scope may be sold as a handle unit 112, 114 with a set of ten or twelve or twenty replaceable shaft/cap unit 110, 120.

III. EXTENDABLE, BENDABLE, OR ARTICULATED CAMERA TIP

Figure 2A:
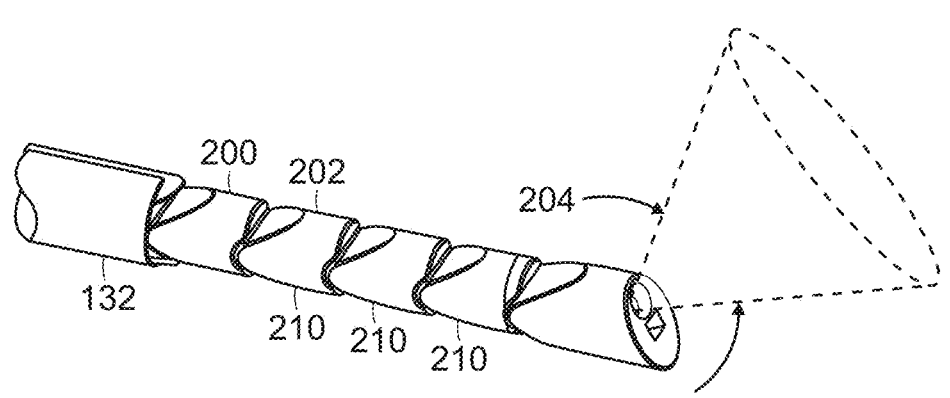
Figure 2B:
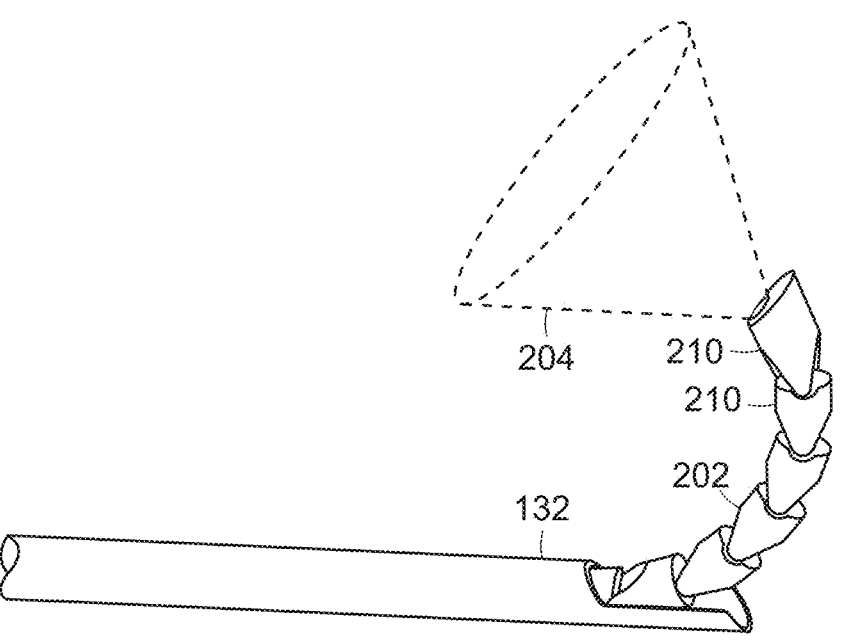
Figures 2C, 2D:
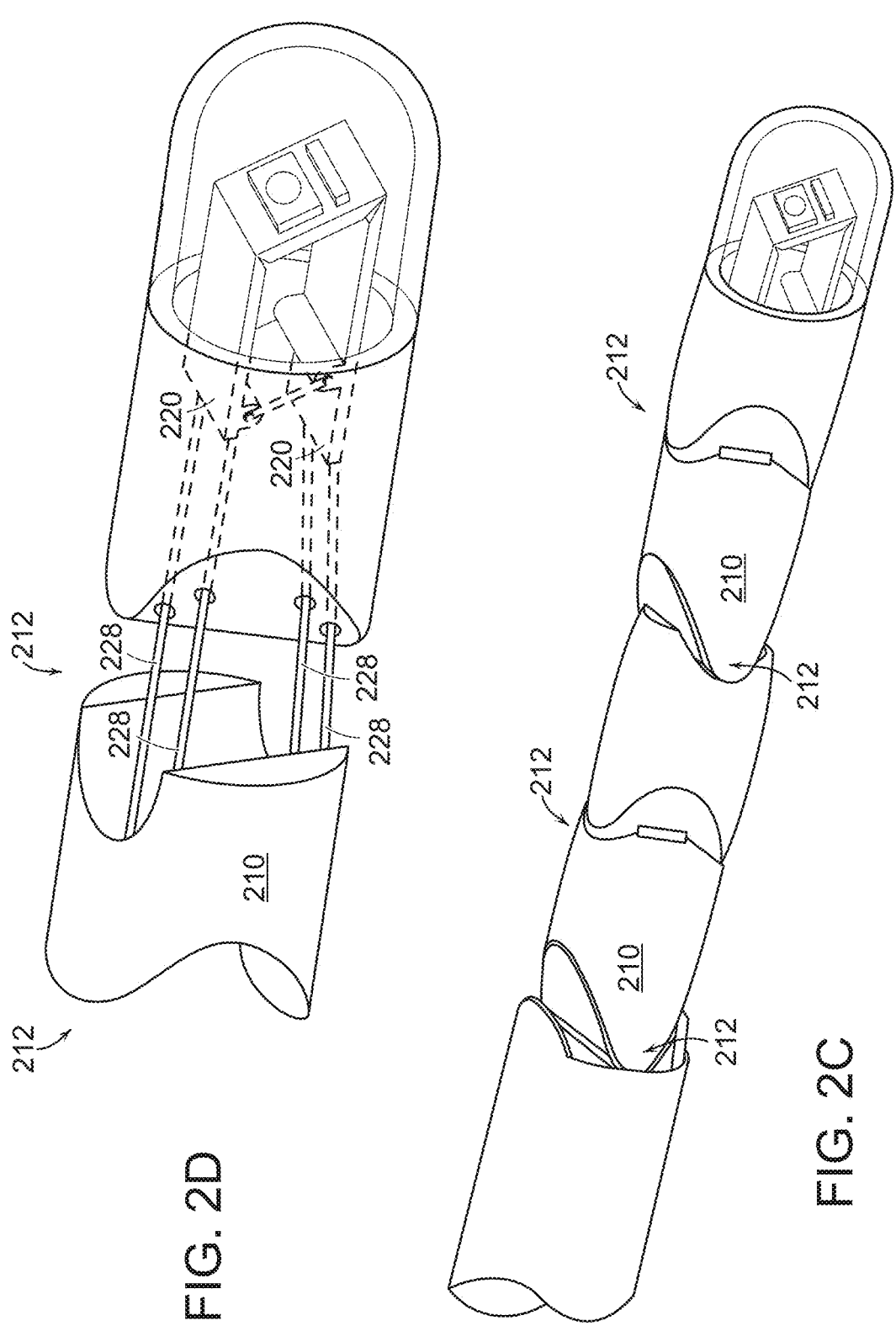

Referring to FIGS. 2A, 2B, 2C, and 2D, the camera tip 202 may be slideable within cannuala shaft 132, to be extendable and retractable. When extended, the distal portion of camera stalk 202 may be bendable, for example, via articulation joints between segments 210. In FIGS. 2A and 2B, cone 204 shows the field of view of the camera. The extendable/bendable portion of shaft 202 may be formed of a series of elements that are each essentially rigid in the longitudinal dimension, but articulated at each joint to permit bending or flexure. The articulation may all be in the same dimension, as shown in FIGS. 2A and 2B. Alternatively, as shown in FIGS. 2C and 2D, articulation pivots 212 may be at alternating 90° angles, so that the bending may be in two dimensions, which in combination, may yield 360° of bending angles. Alternatively, the bendable portion 202 may be formed of elastic material, with an internal stiffener that is relatively stiff and incompressible against longitudinal compression dimension, and flexible in lateral and/or inclination bending. Bendable portion 202 may include two or four cable channels spaced around an outer surface, so that tension cables may cause bending in a desired direction.

Figures 2E, 2F, 2G, 2H:
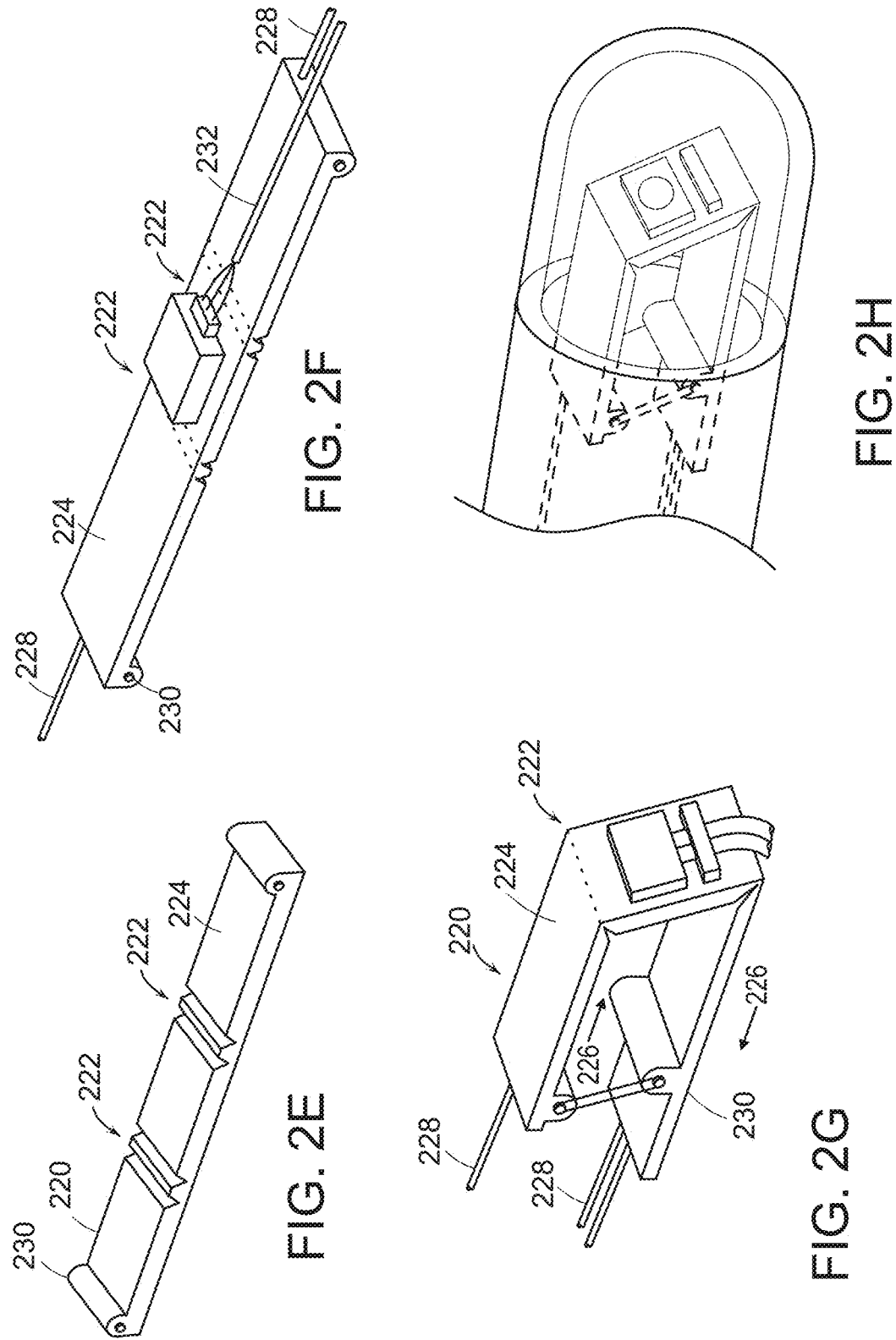
FIGS. 2E, 2F, 2G, and 2H are perspective views of components of an endoscope.

Referring to FIGS. 2E, 2F, 2G, and 2H, in some cases the camera may be pannable within the endo scope tip. For example, the camera and its illumination LED may be mounted on one side of a substrate 220 formed as three rigid segments with two hinges 222, so that the two outer segments 224 may be moved relative to each other 226, and the center segment rotates in place, in the manner of a flexing parallelogram. The two outer segments 224 may be mounted in slide channels, and connected by cables 228 to controls at the handle. Referring to FIG. 2E, substrate 220 may be molded onto a flat flexible backing. The backing may contain folds 222 to create hinge points that allow the backing to fold into its parallelogram configuration (FIGS. 2G and 2H). Pivot points 230 may be molded into substrate 220. Referring to FIG. 2F, a flex circuit 232 may be laminated onto the substrate, and control tension cables 228 attached to the two ends. A camera, illumination LED, pressure sensor, temperature sensor, or other sensors may be affixed to substrate 220. Referring to FIG. 2G, substrate 220 may be folded into three sides of a parallelogram, and a fourth side may be formed by a linkage connected to hinge points.

Longitudinal movement 226 of one face of the substrate relative to the other changes the angle of the center segment, and thus the angle of the image CCD or other camera, and any other sensor. This may provide an adjustable view angle over a range that may be as large as 90°. The endoscope can also accommodate for a 180° or retrograde view where the endoscope has a flat top construction and a rotatable or living hinge rectangular endoscope architecture.

Passages and apertures for ingress and egress of irrigation, inflation, or other fluids may be provided in the tip. An aperture for irrigation fluid may be aimed to clear fouling from a window or lens over the camera.

At least one of surfaces 224 may contain a metal strip bonded onto or into segment 224. The metal strip may be a spring steel or nickel-titanium alloy with a preformed radius of curvature. The metal alloy may alternatively be a malleable metal such as aluminum or may be a nickel-titanium (nitinol) alloy with a shape memory feature. The metal strip allows the elongated core to reliably bend in one plane of curvature. Where the memory substrate is spring-steel or nitinol, it may bend to a shape if malleable, or may be made steerable with a nitinol shape-memory component.

Figures 2I, 2J, 2K, 2L:
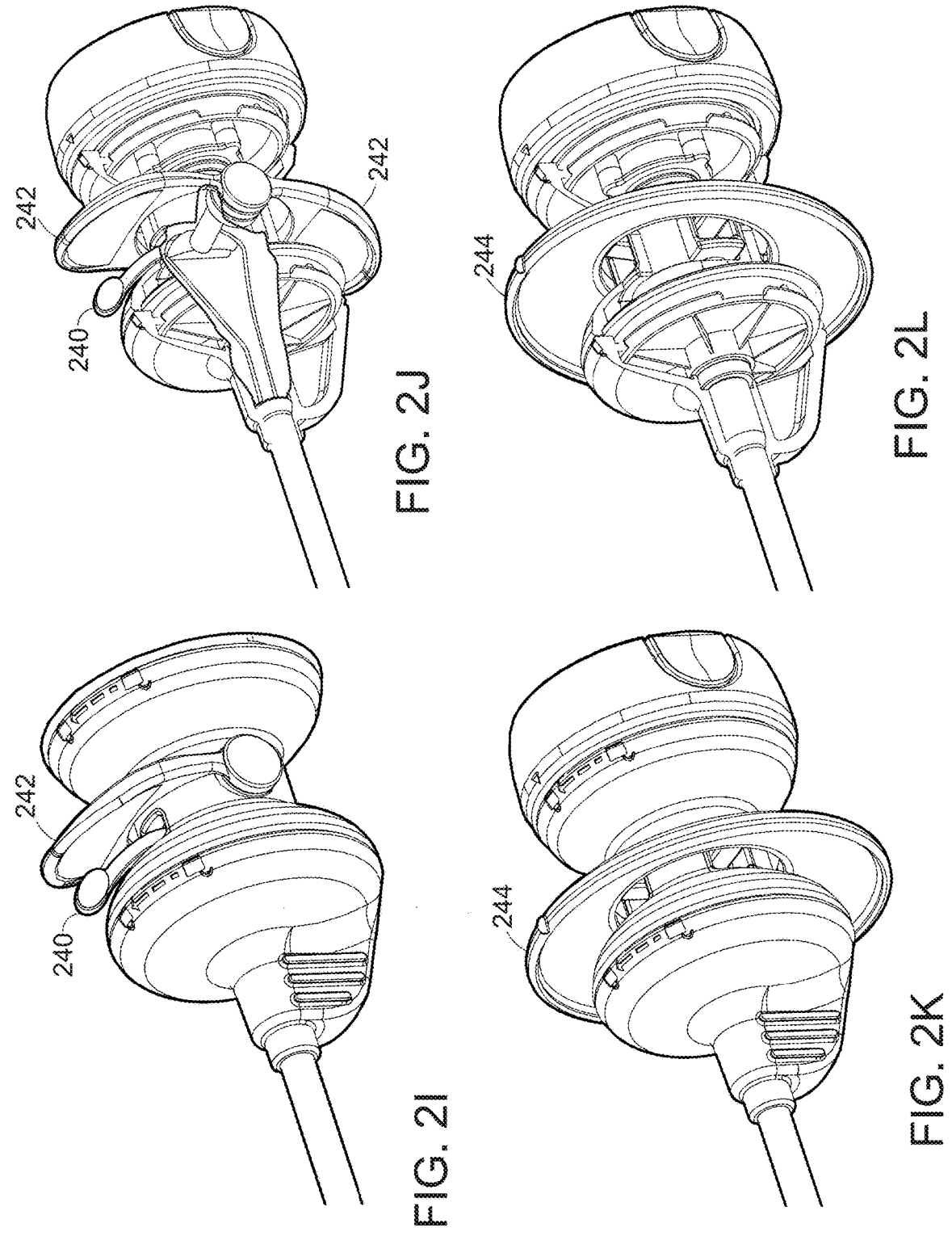

Referring to FIGS. 2I and 2J, lever 240 may be moved to advance/project or retract/withdraw the camera within insertion shaft (FIGS. 2A and 2B). Another switch/lever 242 (for example a paddle-shaped switch) may control cables or levers that flex the articulable tip by exerting tension on cables 228 that extend to the tip, to cause rotational articulation at joints 212 along the extendable portion 202 of shaft 110, thereby to control articulation of the camera tip to move in positive-y and negative-y directions. Another lever may be used to control camera panning (FIGS. 2C, 2D, 2E, 2F, 2G, and 2H).

Referring to FIGS. 2K and 2L, a four-point control 244 may control four control cables 228 or rods or other load bearing components to the articulated or bendable portion of the extendable/retractable and/or articulated camera shaft 202, so that the camera tip may be articulated in positive-x, negative-x, positive-y, and negative-y directions.

Referring again to FIGS. 1D and 1E, the extendable/retractable and/or articulated camera shaft 110, 200 may be used with a reusable handle, disposable tip configuration. The extendable/retractable and/or articulated camera shaft may be used with a reusable or single-use unibody scope configuration.

The articulated camera tip 200 may be especially useful in abdominal thoracic laparoscopy. Typically, during abdominal surgery, the abdominal cavity is inflated with carbon dioxide, to give the surgeon a large open field of view. This gives an extendable/retractable and/or articulated tip space to move. The extendable/retractable and/or articulated tip may be useful to provide a view behind an organ, such as the stomach or liver. If the surgeon only has a fixed view endoscope/laparoscope, the only way to obtain a view behind an organ would be to open another port from the opposite side of the body.

IV. ADDITIONAL FEATURES OF AN ENDOSCOPE

Referring to FIG. 1B, disposable shaft portion 110, 120 may in turn be separable into an outer cannula 132 for protection and strength, and an inner shaft portion 134 carrying various illumination, optical, and fluid-carrying componentry. Illumination may be provided by an LED at or near the distal tip, or via fiber optics from an illumination source in the handle.

Referring again to FIG. 1A, the endoscope may have a handle 112, 114, 120, and a shaft 110 for insertion into a body. At or near distal tip 116 of the shaft 110 may be a camera, electronic image sensor, or other optical component. The camera's orientation may be fixed in the scope, or may be pannable. The camera may be at tip 116, looking out from the shaft, or may be recessed a short distance behind the structural tip of the shaft. Also at or near the tip may be an illumination source, such as an LED. Tip 116 may have a rigid pointed tocar tip, or may have a spoon-shaped portion that reaches past the image sensor, or may be flexible (in the manner of the tip of a colonoscope), in each case extending a little beyond imaging camera to provide physical protection to the camera/image sensor during insertion or to protect the camera/image sensor from a surgical cutting device.

Illumination may be in visible light, infrared, and/or ultraviolet. In some cases, the illumination LED (light emitting diode) may be placed in reusable handle 112, 114, and the disposable shaft may have fiber optics to transmit light to the tip, and joint 130 may have an optical coupler. In other cases, the illumination LED may be placed in tip 116 to illuminate the surgical cavity directly; in such cases, joint 130 may have a power connector. In some cases, the LED may be recessed from the tip, or placed somewhere in the shaft, and optical fiber may carry illumination light to the tip. The optical fiber may be configured, for example, with a split, so that light will be arrayed in a desired pattern around the image sensor to better distribute the light into the surgical cavity around the image sensor.

The shaft 110 itself may be rigid, made of a nonbioreactive metal such as stainless steel or coated aluminum. In some cases, a surgical cavity around the endoscope tip may be insufflated by gas (typically carbon dioxide), or irrigated by saline solution. In either case, fluid inflow and outflow may be effected by channels through the shaft.

Shaft 110 may also carry power wires to the illumination LED and the camera, and carry signal wires that carry an optical signal back from the camera to electronics in the reusable portion 112, 114 of the handle. Electrical power to the camera may be supplied over conductors in a flexible cable or on a printed circuit board (flexible or rigid), and insulated with a conformal and insulating coating such as parylene. This same flexible circuit board may have signal conductors for the video signal from the camera. The video signal may be transmitted from the camera to the handle using any video signal protocol, for example, MIN (Mobile Industry Processor Interface) or HDMI. Parylene may also improve biocompatibility.

Shaft 110 may also carry cables or other mechanical elements to control panning of the camera.

Referring to FIG. 3A, rotation collar may have various features that make rotation easy. For example, depressions 302 may provide a good grip for fingers for light roll torque. Fin 304 may provide greater leverage for greater roll torque, and may also provide a fixed rotational point of reference.

A button 310 may perform various functions, such as turning illumination LED on or off, taking pictures, starting and stopping video, and the like. A single button may perform all these functions based on the nature of the press. For example, press-and-hold for 3 seconds may turn the illumination LED on and off. A quick press may capture a single-frame still picture. A double-click may start and stop video recording.

If the camera at the tip 116 of shaft 110 is pannable or has other controllable features, there may be a control (for example, a lever, or a touch-slide panel, etc.) near button 310 to control that adjustment of the camera.

Figure 3C:
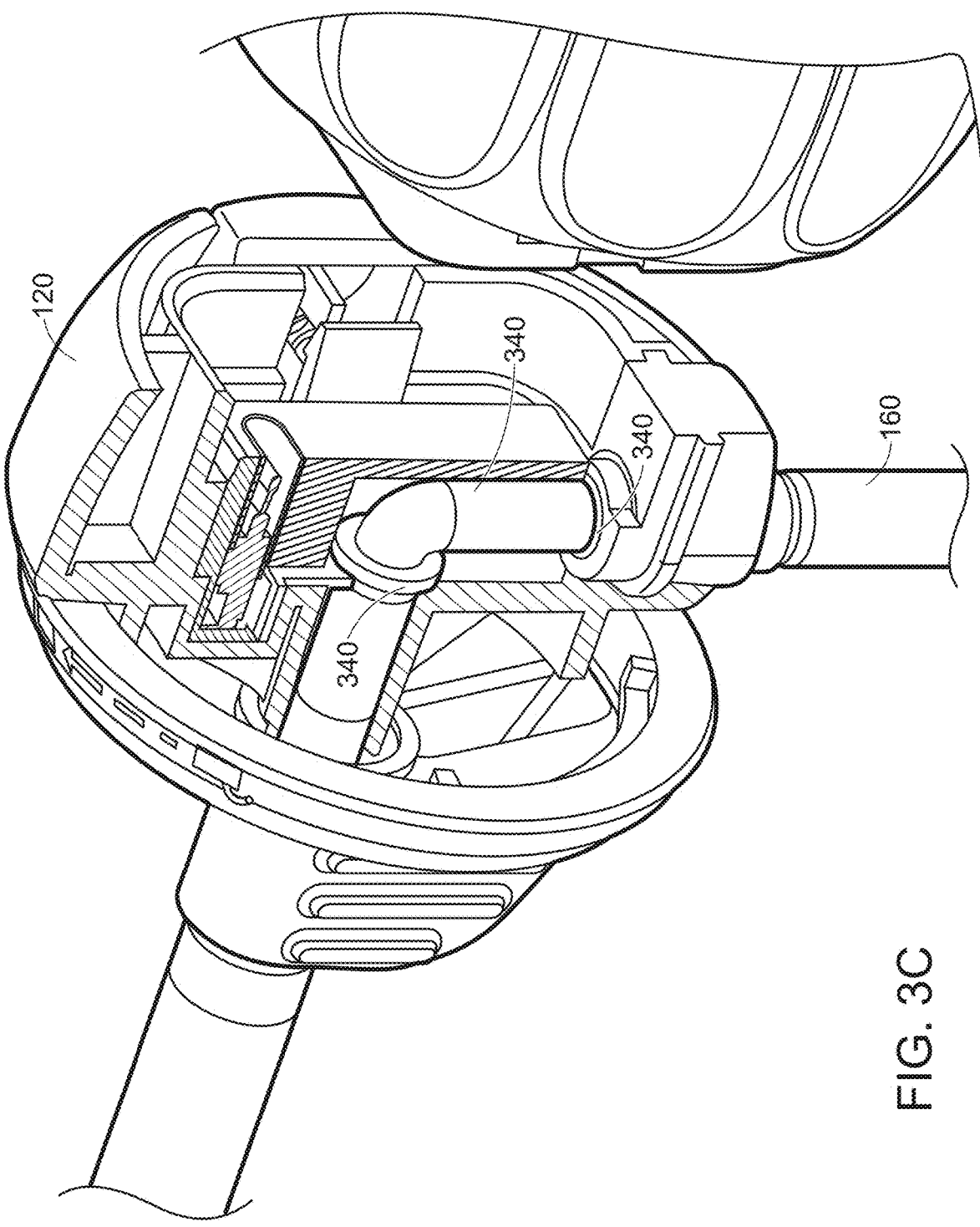
Figure 5A:
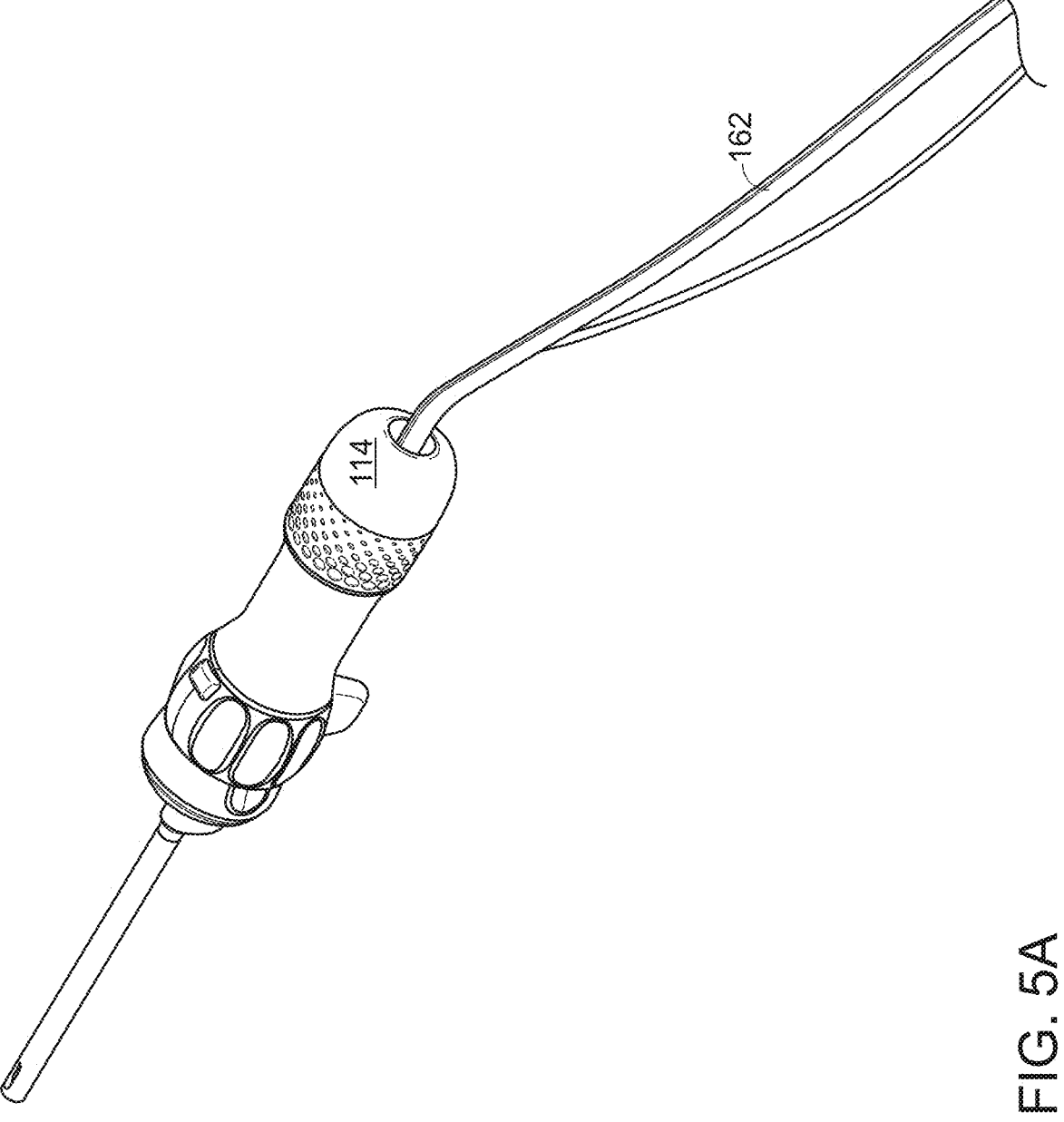
Figure 5B:
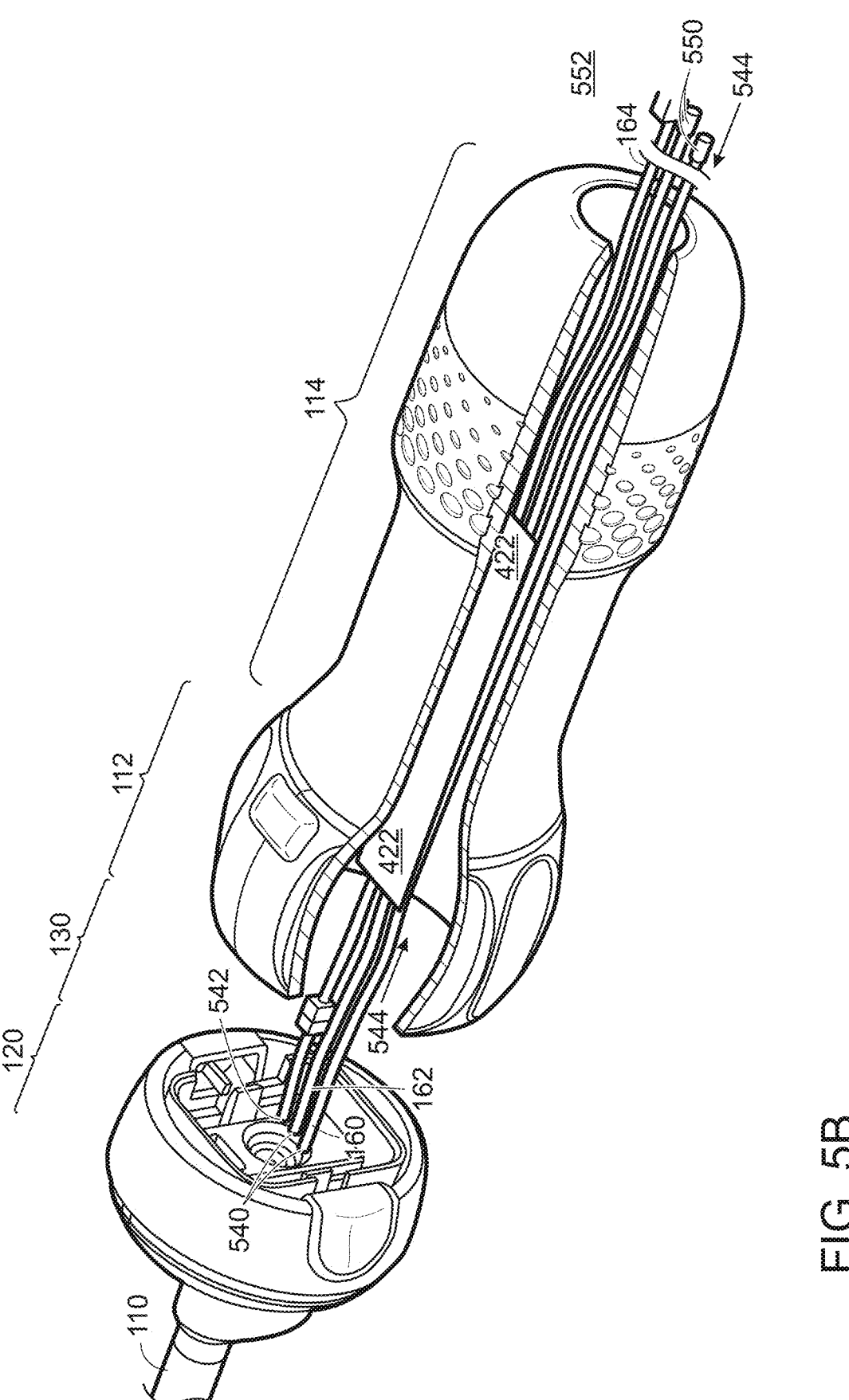

One or more ultraviolet LEDs may be placed inside handle 112,114, inside shaft 110, or near tip 116 to assist with insuring sterility of the internal components of the device or of the water as it passes thru the device Referring to FIG. 3C, irrigation/insufflation hose(s) 160, 162 may enter at various points through the handle. For example, irrigation/insufflation hose(s) 160, 162 may enter through fin 304. Or, as shown in FIGS. 5(a), and 5(b), irrigation/insufflation fluid/gas hose(s) 160, 162 may enter through the proximal end of handle 114. This hose may then be disconnectable via a fluid disconnect joint 320 within joint 130. Referring to FIG. 3(c), in cases where hose(s) 160 for insufflation fluid/gas enters through disposable cap 120, various joints and strain relief features 340 may be used to hold hose(s) 160 in place.

Figure 3D:
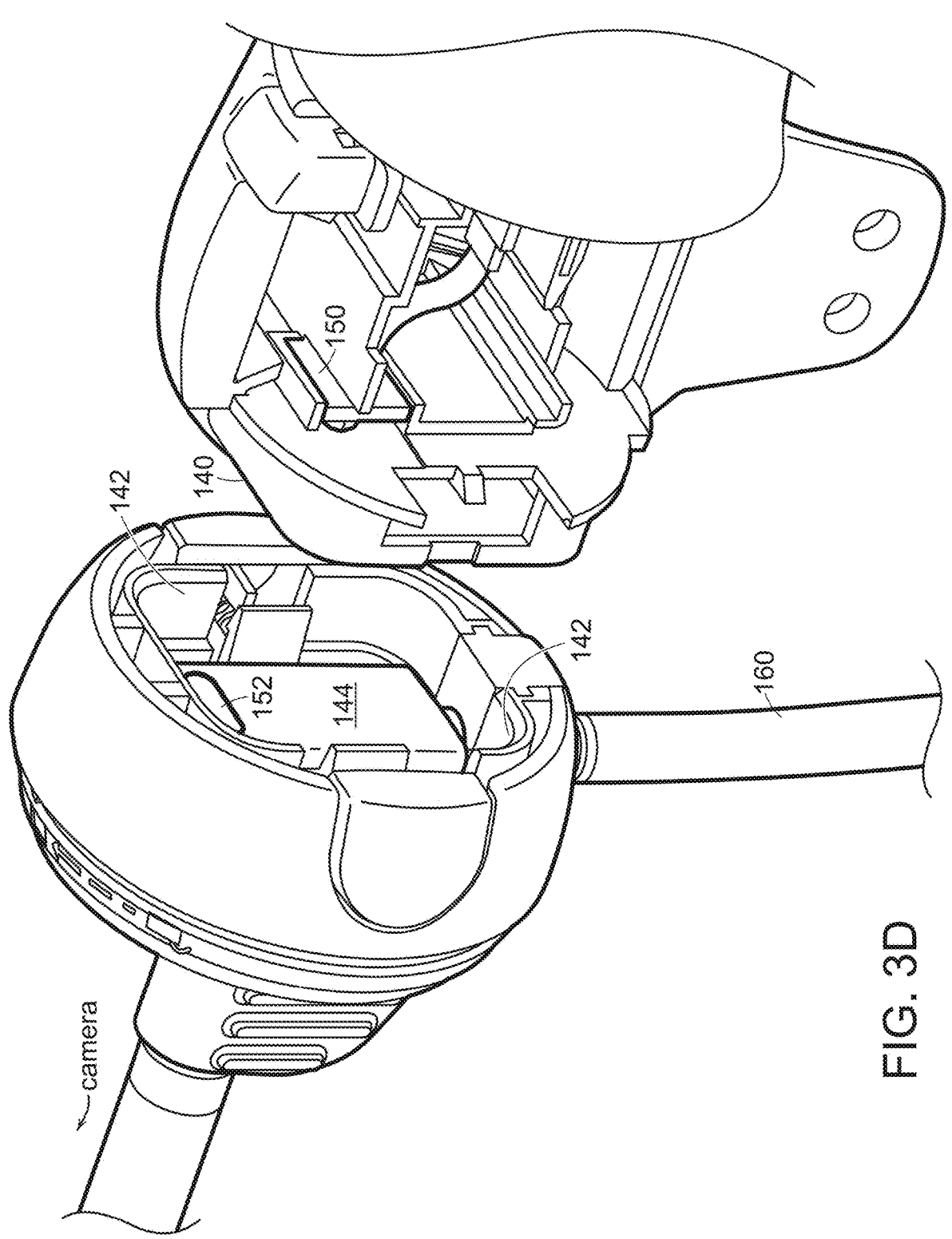
Figure 3E:
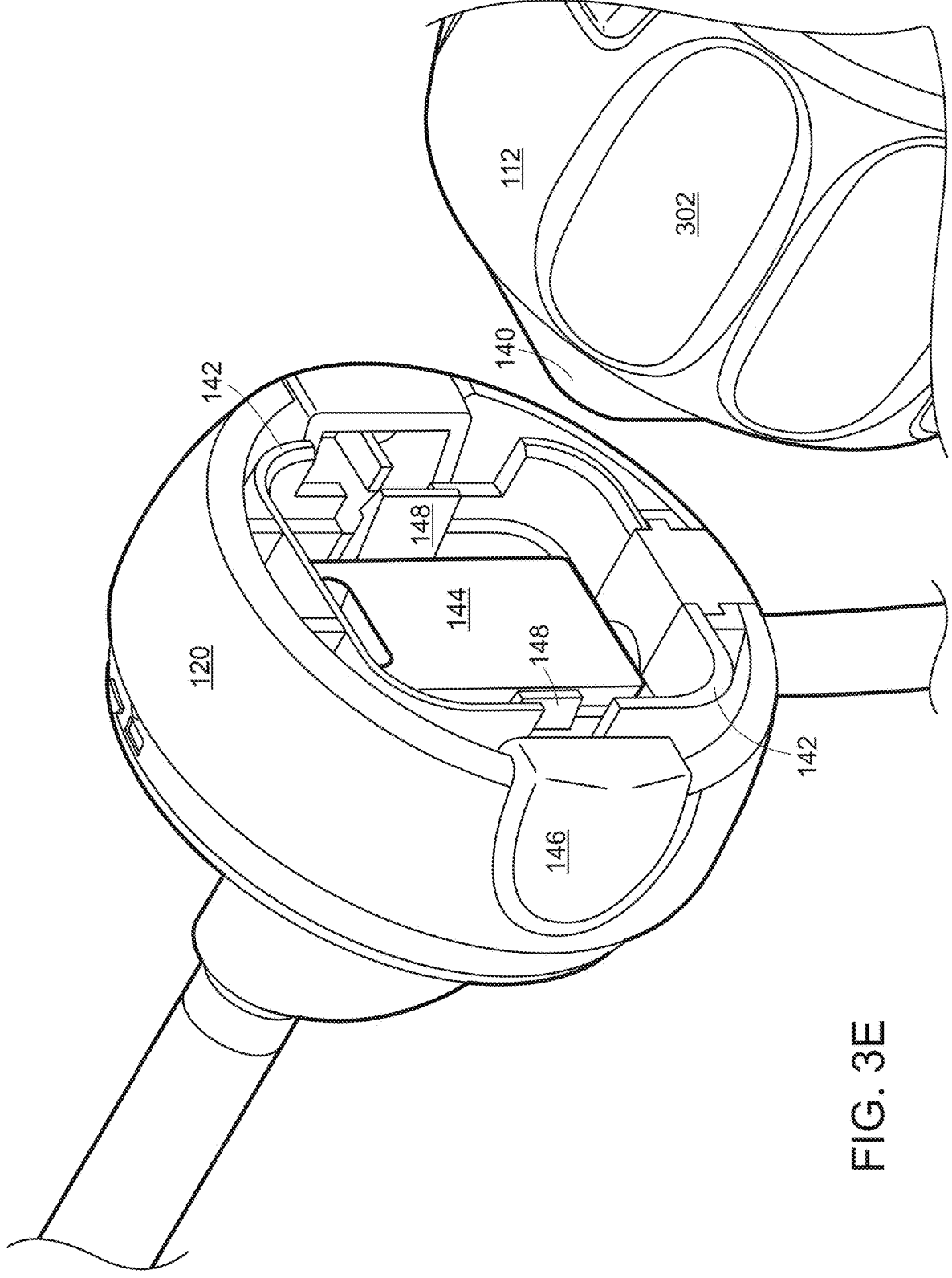
Figure 3F:
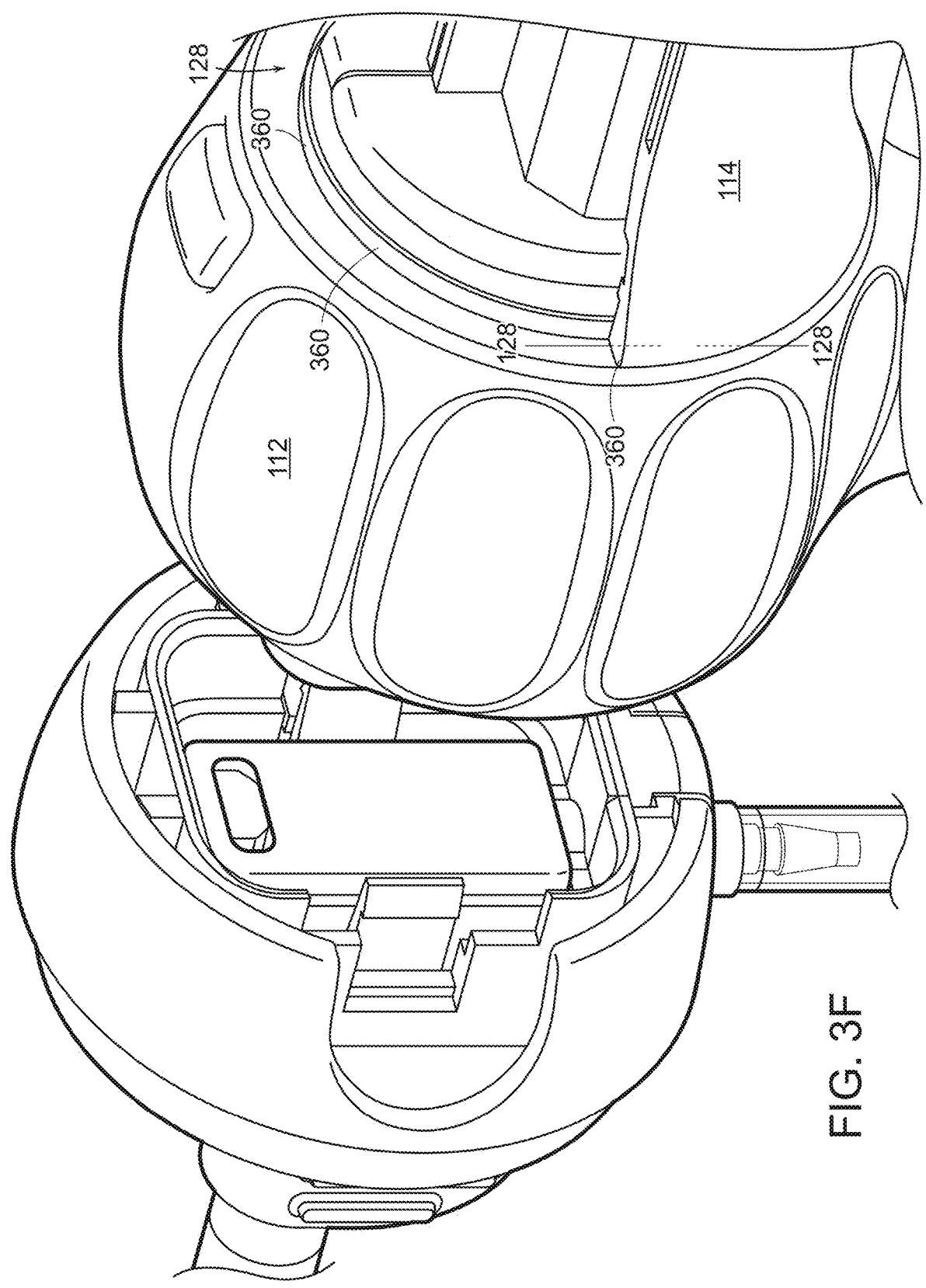
Figure 3G:
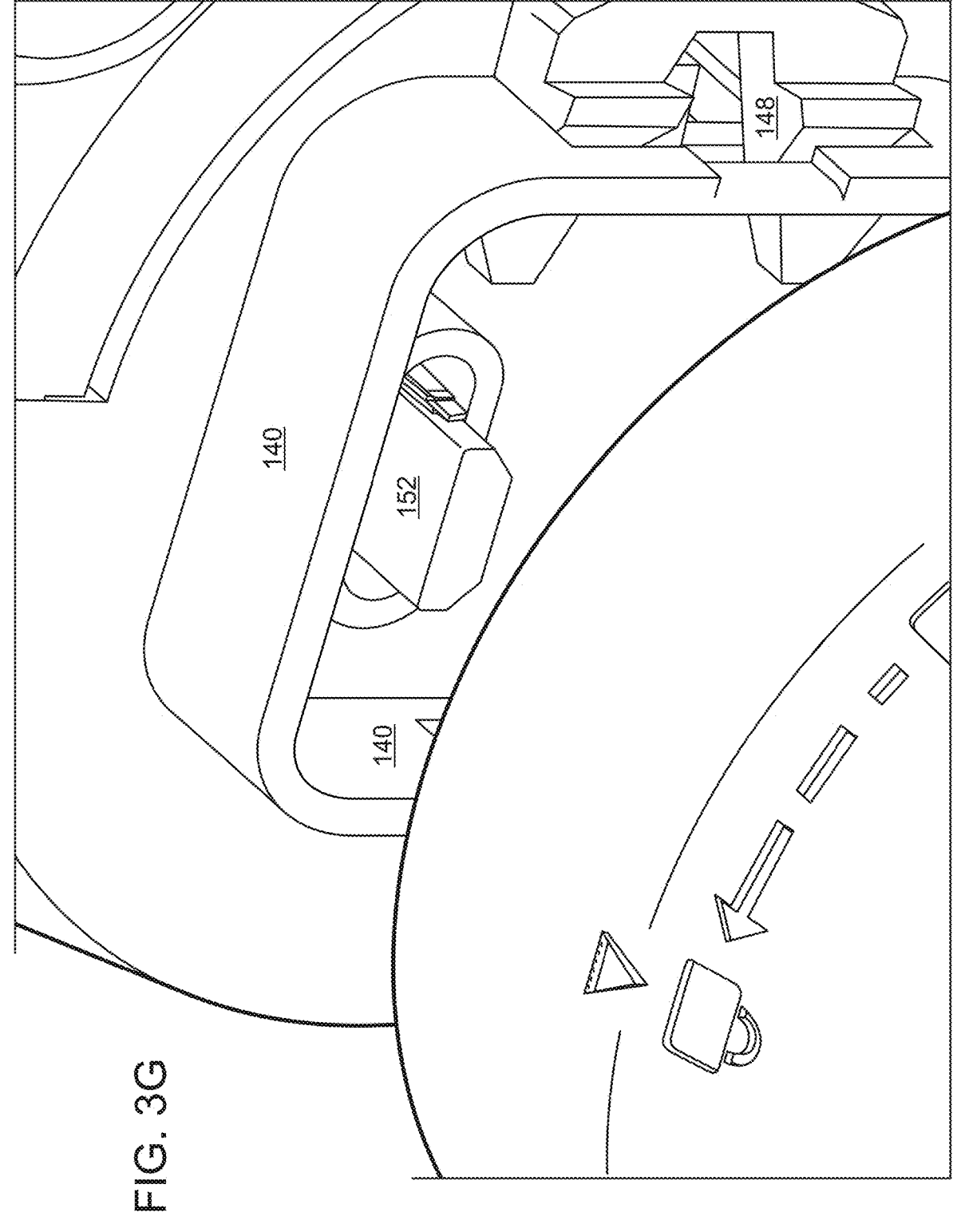

Referring to FIG. 3D and FIG. 3G, electrical connectors 150, 152 such as USB-C or mini-HDMI connectors may be used to connect the camera to a circuit board interior to handle 114.

Referring to FIG. 3E, rotation-locking coupling 140, 142 may lock disposable cap 120 in rotational relationship to rotation collar 112. Various rigid and resilient features 144, 148 may lock them together for other forces and torques, and release buttons 146 may permit them to disengage to allow replacement of disposable cap 120. The coupling between cap portion 120 and rotation-locking coupling 140, 142 may place much of the stress at the periphery of the joint, so that joint 130 may carry and transmit forces (especially torques) well.

Referring to FIG. 3F, rotation between the handle's stationary portion 114 and rotation collar 112 may be provided via a rotational bearing 360 at joint 128.

Figure 4A:
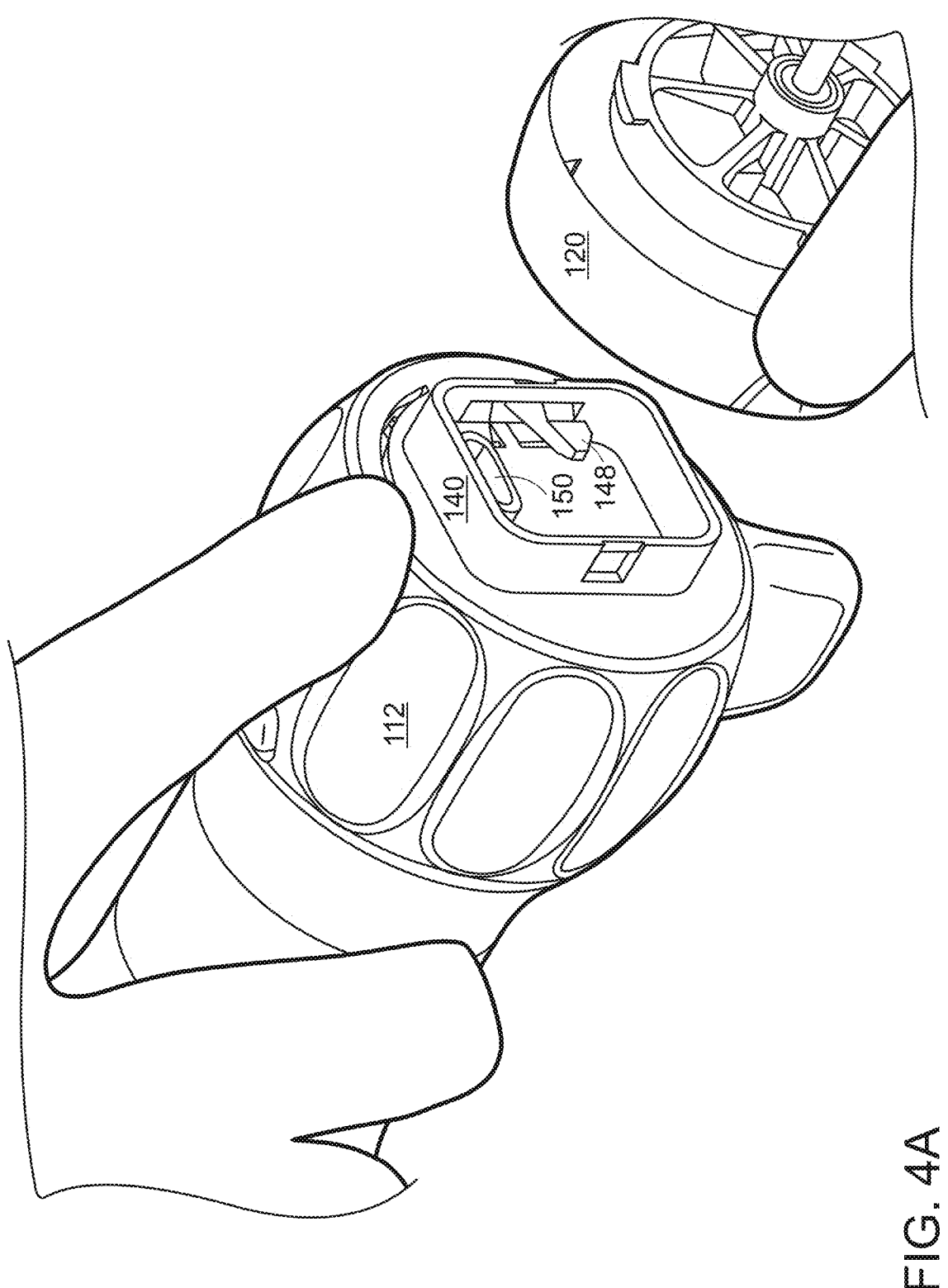
Figure 4B:
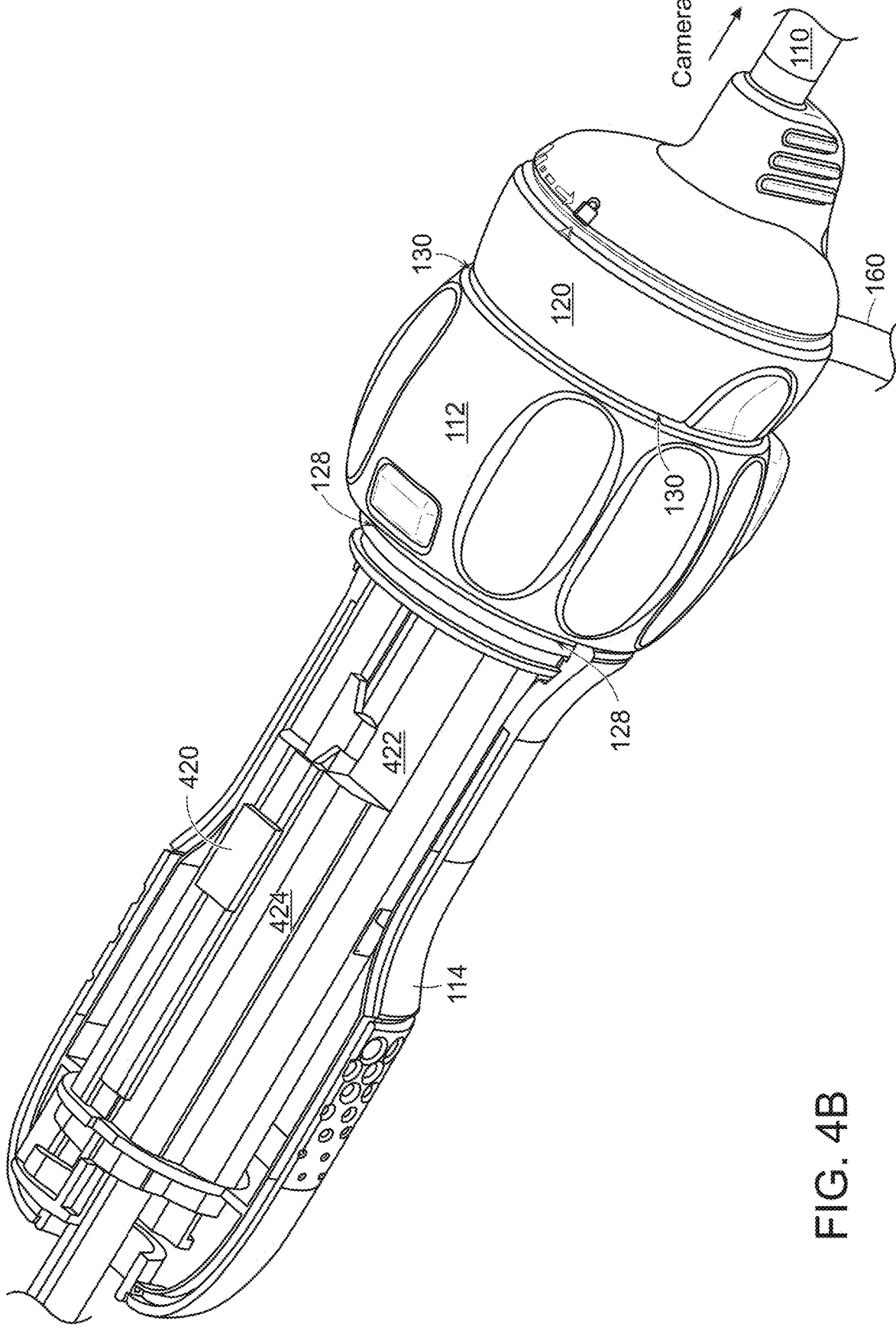
Figure 4C:
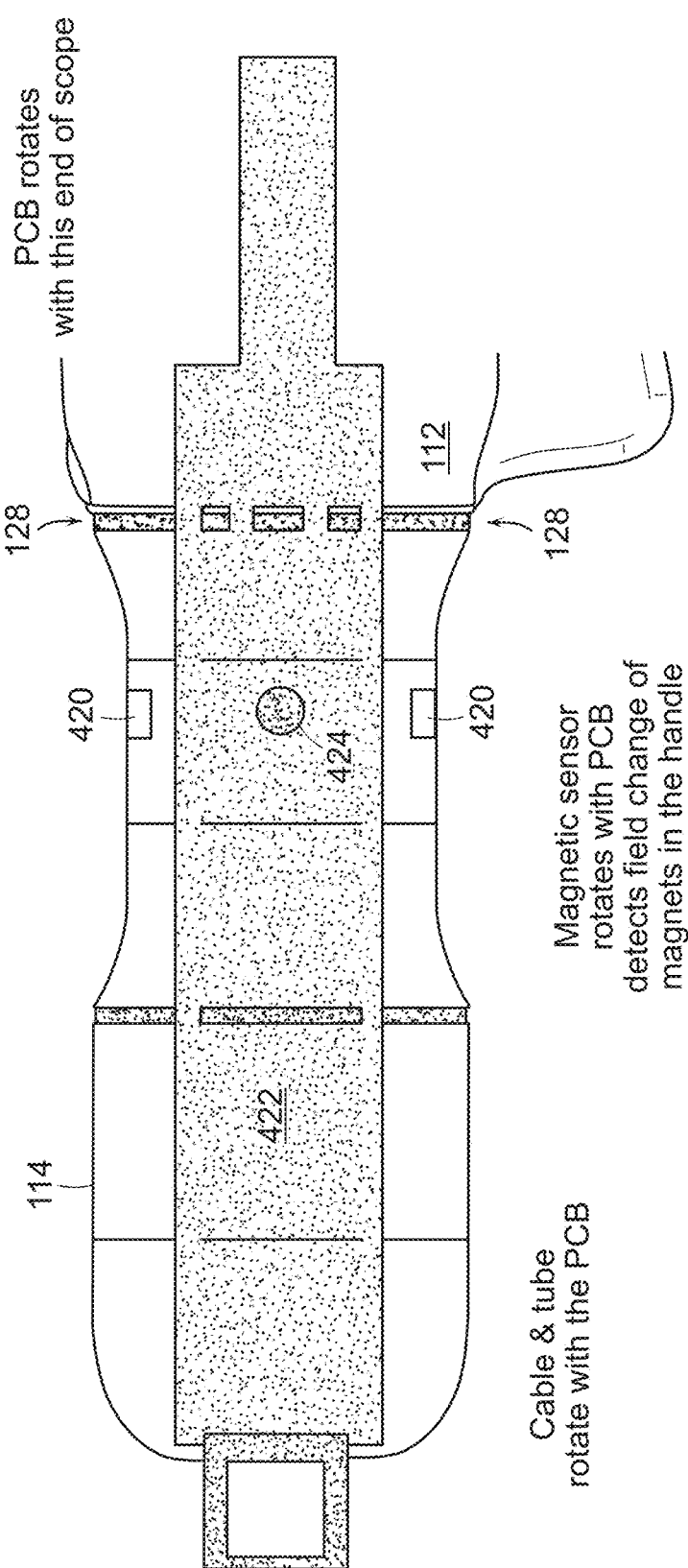
Figure 4D:
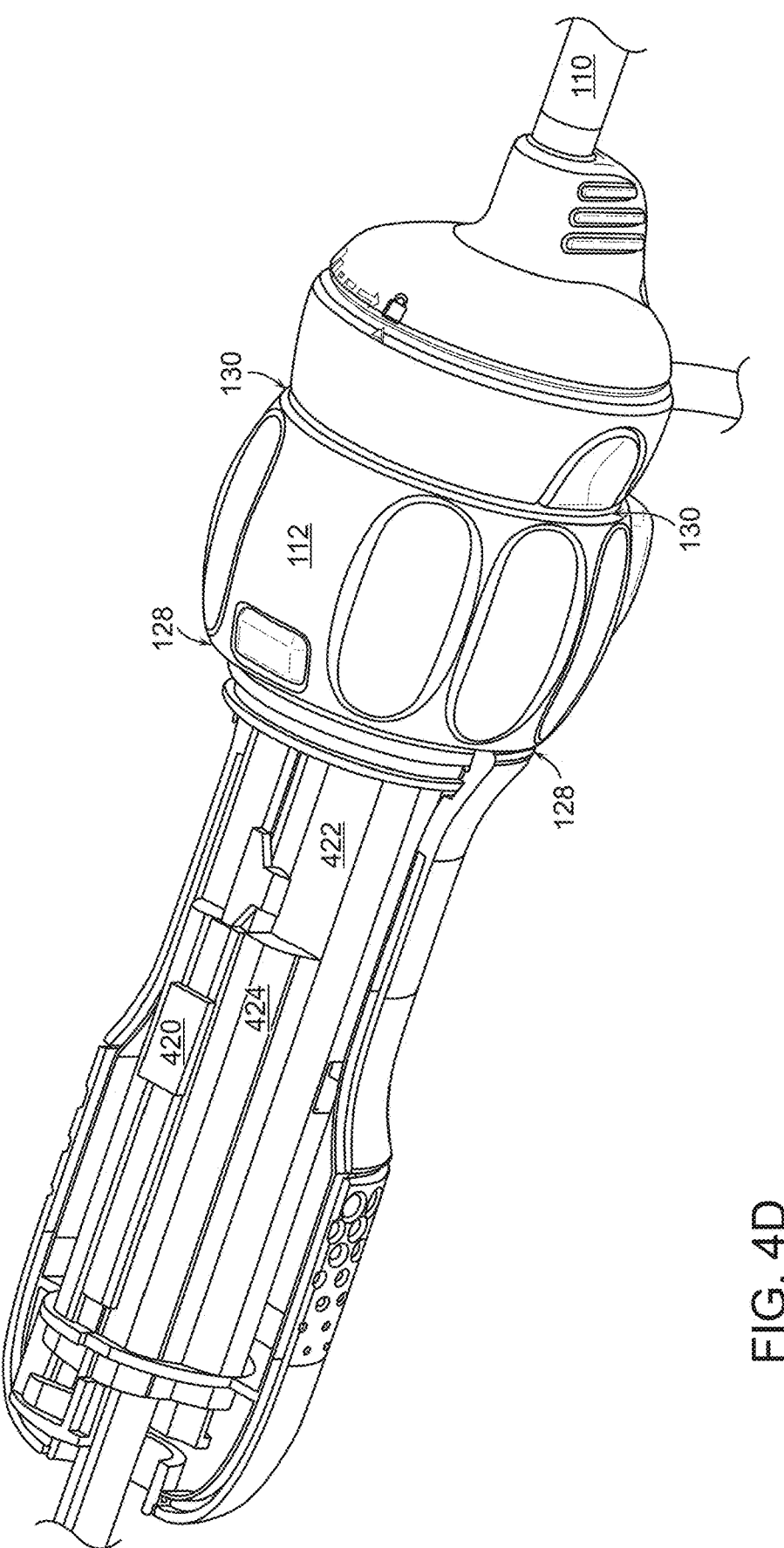

Referring to FIGS. 4B and 4C, proximal handle 114 may contain a number of components, typically components that have only incidental patient contact (and therefore present less risk of cross-infection), are higher in cost (and therefore desirably reusable), and either sterilizeable or may be covered by a sterility sleeve. For example, proximal handle 114 may hold power transformers, signal amplifiers, controls for the illumination LED and camera, a mechanical control for panning the camera, rotation sensors for righting of an image from the camera, and the like. The handle may also include connections to external sources and destinations of power, signal, fluid, and the like.

Proximal handle 114 may include rotational sensors so that an angular orientation of the camera may be ascertained. For example, the inner surface of proximal handle 114 may mount one or more magnets 420, and printed circuit board 422 (which rotates with rotation collar 112 and disposable cap 120) may have sensors 424 that detect the magnets. This may be used to compute a rotational orientation, which may in turn be used to "right" the image from the camera on a video display screen.

The distal tip of the shaft, the camera mounted therein, and the mounting of componentry within the shaft may be designed to be robust. Occasionally, during surgery, the tip of the endoscope may come into contact with a shaver, ablation probe, or cauterization probe, and it may be desirable to have the tip be robust to such contacts. To reduce risk that componentry may be dislodged and left in the patient, the disposable shaft and its componentry may be designed to avoid joints that are at high risk of mechanical failure. A disposable optical system may prevent the image degradation that occurs when nondisposable optics are reused in multiple surgical procedures.

Endoscopes as a genus include arthroscopes, laparoscopes, colonoscopes, and other specialized scopes for various body cavities. For an arthroscope for joint surgery, the shaft may be as small as 5 mm, 5.5 mm, or 6 mm, and highly rigid. For other endoscopes, such as a colonoscope, the diameter may be larger, and the shaft may be flexible.

The endoscope may be delivered as a handle and multiple tips, each tip individually sealed for sterility.

Referring to FIG. 5B, hoses 160, 162 for irrigation/insufflation fluid/gas in, irrigation/insufflation fluid/gas out, and electrical connection cord 164 may be permanently affixed 540, 542 to disposable cap 120. This arrangement may allow that hose 162 that carries water out of the surgical cavity, and which is therefore contaminated, may be disposable, and no fluid will come into contact with the reusable part 114 of the handle. Hoses and cord 160, 162 may be routed through channel 554 running the length of reusable handle 112, 114. Channel 544 may be of inner diameter large enough to permit easy passage of hoses and cord 160, 162, 164, and connectors 550, 552, and have a continuous smooth wall that permits easy sterilization, to permit ready replacement of the replaceable components. Channel 554 may be off the central axis, to allow printed circuit board 422 to lie on the central axis. Connectors 550, 552 at the end of hoses and cords 160, 162 may be small enough to pass through channel 554. Thus, replacement of shaft 110, cap 120, hoses and cords 160, 162 may be effected by threading connectors 550, 552 and hoses and cord 160, 162 through channel 544. Electrical cord 164 may have a connector 554 at or near joint 130, and hose(s) 160 for irrigation/insufflation fluid/gas flowing into the surgical cavity may likewise have a connector at joint 130 to allow this hose(s) to be reusable, or may be permanently affixed 540 to reduce possibility of leaking. Having hoses and cable 160, 162 roughly on-axis reduces undesirable cable flop as the scope is in use, and reduces undesirable torque on cap 120. Forming shaft 120, cap 120, and hoses 160, 162 as an integral unit for replacement reduces possibility of leaking, and improves sterility of the replacement operation.

Figure 6:
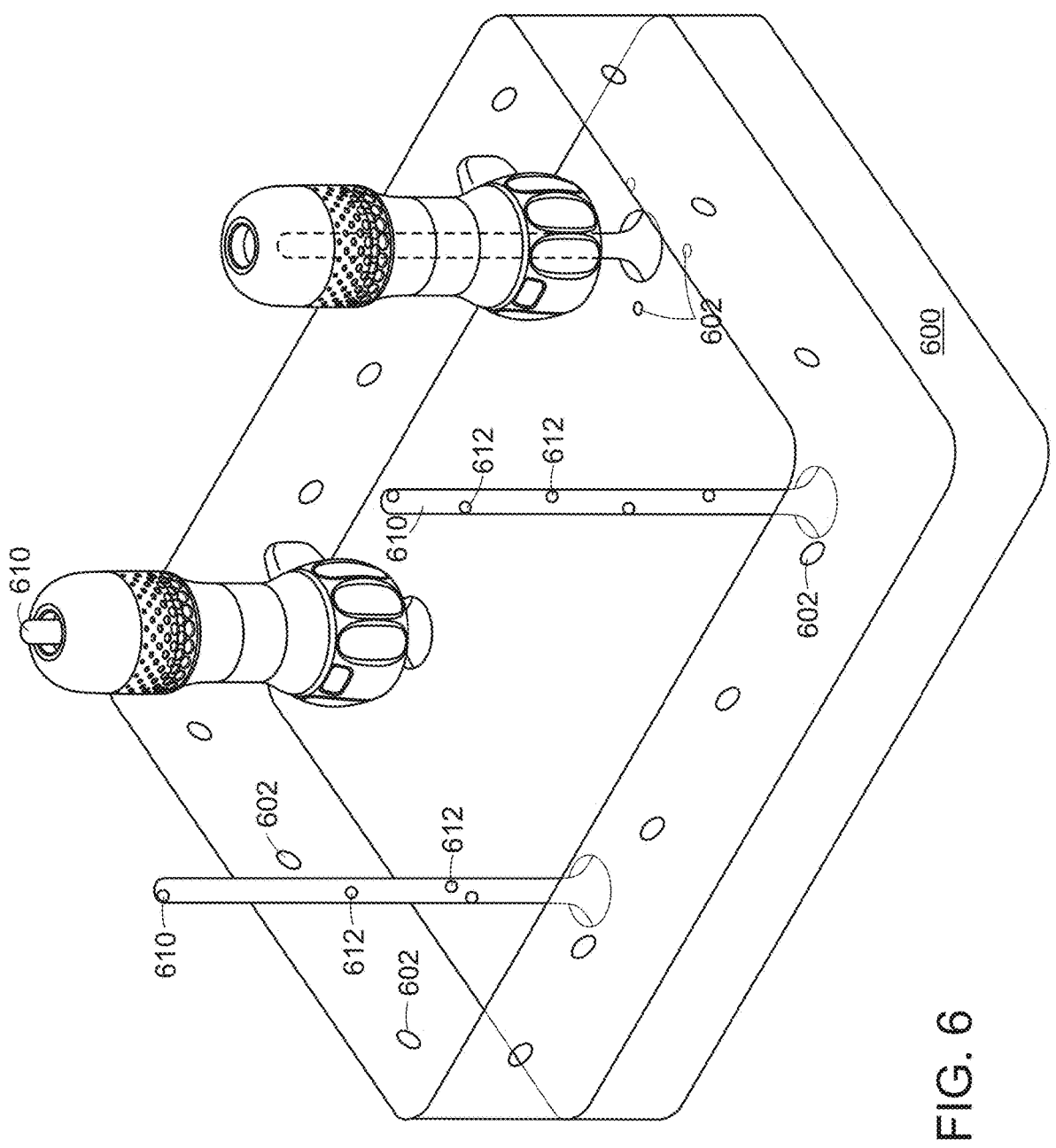
FIG. 6 is a perspective view of endoscope handles in a sterilizer.

Referring to FIG. 6, reusable handles 112, 114 may be sterilized in a sterilizer 600. Preferably, hose(s) 160, 162 and all other portions of endoscope 100 that come into contact with the patient, or with fluids that have come into contact with the patient, are disposable, and the design for reusable portions 112, 114 ensures that contamination is minimized through avoiding contact with the patient's bodily fluids. Sterilizer 600 may be arranged to accept one or more reusable handles 112, 114, and irradiate them with ultraviolet light from ultraviolet LEDs 602. Rods 610 that pass through handle channel 544 may have ultraviolet LEDs 612 arranged along their lengths, to sterilize internal channels 544.

V. OTHER EMBODIMENTS

Embodiments of the invention may include any one or more of the following features, singly or in any combination. An insertion shaft of an endoscope tip has a rigid proximal portion and a distal portion. The distal portion is bendable to direct a field of view of imaging circuitry in a desired direction. An illuminator and solid state imaging circuitry are at or near a distal tip of the articulable distal portion. The illuminator is designed to illuminate, and the imaging circuitry being designed to capture imaging of, an interior of a body cavity for a surgeon during surgery. A coupling of the replaceable endoscope tip is designed to separably connect the insertion shaft at a joint to a handle portion, and to disconnect the joint. The coupling has mechanical connectors. When the joint is separated, the mechanical connectors permit removal of the insertion shaft from the handle for disposal and replacement. When the joint is connected, the joint is designed to provide mechanical force transfer between a surgeon's hand to the insertion shaft. Electrical connectors are designed to connect the insertion shaft to electronics in the handle. The handle electronics are designed for drive of the illuminator and to receive imaging signal from the imaging circuitry, the handle being designed to permit sterilization between uses. Control force transfer elements are designed to permit a surgeon to direct a direction of the imaging circuitry by transfer of mechanical force directed by a surgeon to the articulable distal portion. The distal bendable portion includes a series of articulated rigid segments. A sheath or cover over the articulated rigid segments is designed to reduce intrusion or pinching. The distal bendable portion is formed of a solid component, bendable in its lateral and elevation dimensions, and relatively incompressible in compression in its longitudinal dimension. The distal bendable portion is extendable from and retractable into a solid sheath. The distal bendable portion is bendable in one dimension. The distal bendable portion is bendable in two orthogonal dimensions. The imaging circuitry is mounted within at or near a distal tip of the articulable distal portion via a pannable mounting. The pannable mounting is designed as two sides of a parallelogram. The imaging circuitry is mounted on a structural segment hinged to the two parallelogram sides. Passages and apertures are designed to pass irrigation fluid to improve view from a lens or window over the imaging circuitry. Passages and apertures are designed to pass inflation fluid to enlarge a cavity for surgery. Mechanical connectors of the coupling include a twist-lock designed to affix the endoscope insertion shaft to the handle portion. A plurality of the endoscope tips are bundled and packaged togeterh with a handle. The handle has electronics designed for drive of the illuminator and to receive imaging signal from the imaging circuitry. The plurality of tips and handle are packaged for integrated shipment and sale. The illuminator is an illumination LED mounted at or near the distal tip. The illuminator is an emission end of a fiber optic fiber driven by an illumination source in the handle.

Various processes described herein may be implemented by appropriately programmed general purpose computers, special purpose computers, and computing devices. Typically a processor (e.g., one or more microprocessors, one or more microcontrollers, one or more digital signal processors) will receive instructions (e.g., from a memory or like device), and execute those instructions, thereby performing one or more processes defined by those instructions. Instructions may be embodied in one or more computer programs, one or more scripts, or in other forms. The processing may be performed on one or more microprocessors, central processing units (CPUs), computing devices, microcontrollers, digital signal processors, or like devices or any combination thereof. Programs that implement the processing, and the data operated on, may be stored and transmitted using a variety of media. In some cases, hard-wired circuitry or custom hardware may be used in place of, or in combination with, some or all of the software instructions that can implement the processes. Algorithms other than those described may be used.

Programs and data may be stored in various media appropriate to the purpose, or a combination of heterogenous media that may be read and/or written by a computer, a processor or a like device. The media may include nonvolatile media, volatile media, optical or magnetic media, dynamic random access memory (DRAM), static ram, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge or other memory technologies.

Databases may be implemented using database management systems or ad hoc memory organization schemes. Alternative database structures to those described may be readily employed. Databases may be stored locally or remotely from a device which accesses data in such a database.

In some cases, the processing may be performed in a network environment including a computer that is in communication (e.g., via a communications network) with one or more devices. The computer may communicate with the devices directly or indirectly, via any wired or wireless medium (e.g. the Internet, LAN, WAN or Ethernet, Token Ring, a telephone line, a cable line, a radio channel, an optical communications line, commercial on-line service providers, bulletin board systems, a satellite communications link, a combination of any of the above). Transmission media include coaxial cables, copper wire and fiber optics, including the wires that comprise a system bus coupled to the processor. Transmission may occur over transmission media, or over electromagnetic waves, such as via infrared, WiFi, Bluetooth, and the like, at various frequencies using various protocols. Each of the devices may themselves comprise computers or other computing devices, such as those based on the Intel® Pentium® or Centrino™ processor, that are adapted to communicate with the computer. Any number and type of devices may be in communication with the computer.

A server computer or centralized authority may or may not be necessary or desirable. In various cases, the network may or may not include a central authority device. Various processing functions may be performed on a central authority server, one of several distributed servers, or other distributed devices For the convenience of the reader, the above description has focused on a representative sample of all possible embodiments, a sample that teaches the principles of the invention and conveys the best mode contemplated for carrying it out. Throughout this application and its associated file history, when the term "invention" is used, it refers to the entire collection of ideas and principles described; in contrast, the formal definition of the exclusive protected property right is set forth in the claims, which exclusively control. The description has not attempted to exhaustively enumerate all possible variations. Other undescribed variations or modifications may be possible. Where multiple alternative embodiments are described, in many cases it will be possible to combine elements of different embodiments, or to combine elements of the embodiments described here with other modifications or variations that are not expressly described. A list of items does not imply that any or all of the items are mutually exclusive, nor that any or all of the items are comprehensive of any category, unless expressly specified otherwise. In many cases, one feature or group of features may be used separately from the entire apparatus or methods described. Many of those undescribed variations, modifications and variations are within the literal scope of the following claims, and others are equivalent.

The invention claimed is:

1. A replaceable endoscope tip for an endoscope, comprising:

an insertion shaft having a rigid proximal portion and a bendable distal portion, the bendable distal portion being bendable to direct a field of view of imaging circuitry in a desired direction, the bendable distal portion including a series of articulated rigid segments joined by rotatable joints to permit bending of the bendable distal portion, the segments of the bendable distal portion being incompressible in compression in a longitudinal dimension;

an illumination emitter and solid state imaging circuitry at or near a distal tip of the bendable distal portion, the illumination emitter being designed to illuminate, and the imaging circuitry being designed to capture imaging of, an interior of a body cavity for a surgeon during surgery;

a coupling for a separation joint between a proximal portion of a handle and the replaceable endoscope tip, the separation joint designed to separably connect the insertion shaft to the proximal handle portion, the coupling having:

a mechanical connector designed:

to permit separation and removal of the replaceable endoscope tip for disposal and replacement with another replaceable endoscope tip; and to permit connection, the separation joint designed when connected to provide mechanical force transfer applied by a surgeon's hand to the replaceable endoscope tip, the separation joint having features to transfer roll torques, the separation joint having locking features and force-transmittal surfaces at its periphery to transmit insertion and withdrawal forces across the separation joint, the separation joint's locking features and peripheral force-transmittal surfaces designed to provide stiffness in bending across the separation joint to transfer pitch and yaw torques across the separation joint, an electrical connector designed to provide separable electrical connectivity between electronics in the handle and the illumination emitter and imaging sensor, the handle electronics designed for drive of the illumination emitter and to receive an imaging signal from the imaging circuitry, the handle being designed to permit sterilization between uses; and control force transfer elements designed to permit the surgeon to direct a direction of the imaging circuitry by transfer of mechanical force directed by the surgeon to the bendable distal portion to cause the bendable distal portion to bend under the surgeon's control, the control force transfer elements designed to transmit force from a handle of the endoscope to a terminal segment of the bendable distal portion;

the imaging circuitry being mounted within at or near a distal tip of the bendable distal portion via a pannable mounting;

a core within the insertion shaft, the core having two parallel elongated segments, a transverse segment, and two hinges connecting the transverse segment between the two elongated segments, the elongated segments being designed to carry both tension and compression for longitudinal motion of one of the elongated segments relative to the other, the transverse segment lying within the sheath at or near the distal end of the sheath;

the solid state imaging circuit being mounted on the transverse segment and having an imaging surface arranged in a viewing direction of the endoscope, the transverse segment being hinged between the elongated segments such that longitudinal motion of the one elongated segment relative to the other changes the angle of the imaging circuit relative to the longitudinal axis of the insertion shaft.

2. The replaceable endoscope tip of claim 1, further comprising:

a handle to be held by the surgeon's hand, the handle having a directional control with a finger engagement surface, the finger engagement surface designed to accept manipulation by the surgeon's hand to permit the surgeon to direct a direction of the imaging circuitry, the finger engagement surface being at a radius from the central longitudinal axis of the endoscope, and having a lever moment, larger than a radius of the handle, the directional control being generally an arc of a circle.

3. The replaceable endoscope tip of claim 1, further comprising:

a solid and rigid sheath surrounding the bendable distal portion, the bendable distal portion being extendable from and retractable into the solid sheath under control of the surgeon via a control at the handle.

4. The replaceable endoscope tip of claim 1, wherein:

the illumination emitter is a means for emitting illumination; and the control force transfer elements are means for permitting the surgeon to direct a direction of the imaging circuitry by transfer of mechanical force directed by a surgeon to the bendable distal portion to cause the bendable distal portion to bend under the surgeon's control.

5. An endoscope, comprising:

an insertion shaft having a rigid proximal portion and a bendable distal portion, the bendable distal portion being bendable to direct a field of view of imaging circuitry in a desired direction, the bendable distal portion including a series of articulated rigid segments joined by rotatable joints to permit bending of the bendable distal portion, the segments of the bendable distal portion being incompressible in compression in a longitudinal dimension;

a core within the insertion shaft, the core having two parallel elongated segments, a transverse segment, and two hinges connecting the transverse segment between the two elongated segments, the elongated segments being designed to carry both tension and compression for longitudinal motion of one of the elongated segments relative to the other, the transverse segment lying within the sheath at or near the distal end of the sheath;

an illumination emitter and solid-state imaging circuitry at or near a distal tip of the bendable distal portion, the illumination emitter being designed to illuminate, and the imaging circuitry being designed to capture imaging of, an interior of a body cavity for a surgeon during surgery, wherein the imaging circuitry is mounted on the transverse segment within at or near a distal tip of the bendable distal portion via a pannable mounting, the imaging circuitry having an imaging surface arranged in a viewing direction of the endoscope, the transverse segment being hinged between the elongated segments such that longitudinal motion of the one elongated segment relative to the other changes the angle of the imaging circuitry relative to the central longitudinal axis of the insertion shaft;

a handle to be held by a surgeon's hand, the handle having a directional control with a finger engagement surface, the finger engagement surface designed to accept manipulation by a surgeon's hand to permit a surgeon to direct a direction of the imaging circuitry, the finger engagement surface being at a radius from a longitudinal axis of the endoscope, and having a lever moment, larger than a radius of the handle, the directional control being generally an arc of a circle; and control force transfer elements designed to permit a surgeon to direct a direction of the imaging circuitry by transfer of mechanical force directed by a surgeon to the bendable distal portion to cause the bendable distal portion to bend under the surgeon's control, the force transfer elements designed to transmit force from a handle of the endoscope to a terminal segment of the bendable distal portion.

6. The endoscope of claim 5, further comprising:

a coupling for a separation joint between a proximal portion of the handle and the replaceable endoscope tip, the separation joint designed to separably connect the insertion shaft to the proximal handle portion, the coupling having:

a mechanical connector designed:

to permit separation and removal of the replaceable endoscope tip for disposal and replacement with another replaceable endoscope tip; an to permit connection, the separation joint designed when connected to provide mechanical force transfer applied by a surgeon's hand to the replaceable endoscope tip, the separation joint having features to transfer roll torques, the separation joint having locking features and force-transmittal surfaces at its periphery to transmit insertion and withdrawal forces across the separation joint, the separation joint's locking features and peripheral force-transmittal surfaces designed to provide stiffness in bending across the separation joint to transfer pitch and yaw torques across the separation joint, and an electrical connector designed to provide separable electrical connectivity between electronics in the handle and the illumination emitter and imaging sensor, the handle electronics designed for drive of the illumination emitter and to receive an imaging signal from the imaging circuitry, the handle being designed to permit sterilization between uses.

7. The endoscope of claim 5, further comprising:

a solid and rigid sheath surrounding the bendable distal portion, the bendable distal portion being extendable from and retractable into the solid sheath under control of the surgeon via a control at the handle.

8. The replaceable endoscope tip of claim 7, wherein: the finger engagement surface is circular.

9. The replaceable endoscope tip of claim 5, wherein: the bendable distal portion is bendable in two orthogonal dimensions.

10. The replaceable endoscope tip of claim 5, wherein: the series includes at least four segments.

11. The replaceable endoscope tip of claim 5, further comprising:

a flexible sheath or cover over the articulated rigid segments designed to reduce intrusion or pinching.

12. An endoscope, comprising:

an insertion shaft having a rigid proximal portion and a bendable distal portion, the bendable distal portion being bendable to direct a field of view of imaging circuitry in a desired direction, the bendable distal portion including a series of articulated rigid segments joined by rotatable joints to permit bending of the bendable distal portion, the segments of the bendable distal portion being incompressible in compression in a longitudinal dimension;

a core within the insertion shaft, the core having two parallel elongated segments, a transverse segment, and two hinges connecting the transverse segment between the two elongated segments, the elongated segments being designed to carry both tension and compression for longitudinal motion of one of the elongated segments relative to the other, the transverse segment lying within the sheath at or near the distal end of the sheath;

an illumination emitter and solid state imaging circuitry at or near a distal tip of the bendable distal portion, the illumination emitter being designed to illuminate, and the imaging circuitry being designed to capture imaging of, an interior of a body cavity for a surgeon during surgery; the solid state imaging circuitry being mounted on the transverse segment and having an imaging surface arranged in a viewing direction of the endoscope, the transverse segment being hinged between the elongated segments such that longitudinal motion of the one elongated segment relative to the other changes the angle of the imaging circuitry relative to the central longitudinal axis of the insertion shaft;

a handle to be held by a surgeon's hand, the handle having a directional control with a finger engagement surface, the finger engagement surface designed to accept manipulation by the surgeon's hand to permit the surgeon to direct a direction of the imaging circuitry, the finger engagement surface being at a radius about the central longitudinal axis of the endoscope, and having a lever moment larger than a radius of the handle, the finger engagement surface being generally an arc of a circle at a radius about the central longitudinal axis, the directional control further designed to transfer mechanical force from the finger engagement surface to the bendable distal portion to cause the bendable distal portion to bend under the surgeon's control.

13. The endoscope of claim 12, further comprising:
a rigid, solid sheath surrounding the bendable distal portion, the bendable distal portion being extendable from and retractable into the solid sheath.

14. The endoscope of claim 12, wherein: the bendable distal portion is bendable in one dimension.

15. The endoscope of claim 12, wherein: the bendable distal portion is bendable in two orthogonal dimensions.

16. The replaceable endoscope tip of claim 15, further comprising:
a handle to be held by the surgeon's hand, the handle having a directional control with a finger engagement surface, the finger engagement surface designed to accept manipulation by the surgeon's hand to permit the surgeon to direct a direction of the imaging circuitry, the finger engagement surface being circular and having a radius from the central longitudinal axis of the endoscope larger than a radius of the handle.

17. The endoscope of claim 12, further comprising:
a plurality of the replaceable endoscope tips of claim 12; and
a handle with electronics designed for drive of the illumination emitter and to receive an imaging signal from the imaging circuitry; packaged for integrated shipment and sale.

18. The endoscope of claim 12, wherein:
the illumination emitter is an emission end of a fiber optic light path driven by an illumination source distal of the bendable distal portion.

19. The endoscope of claim 12, wherein:
the series includes at least four segments.

20. The endoscope of claim 12, further comprising:
a flexible sheath or cover over the articulated rigid segments designed to reduce intrusion or pinching.

21. The endoscope of claim 12, the rigid segments further enclosing passages for passage of irrigation fluid to improve view from a lens or window over the imaging circuitry.

22. The endoscope of claim 12, the rigid segments further enclosing passages for passage of inflation fluid to enlarge a cavity for surgery.

23. The endoscope of claim 12, further comprising:
a coupling for a separation joint between a proximal portion of the handle and the replaceable endoscope tip, the separation joint designed to separably connect the insertion shaft to the proximal handle portion, the coupling having:
a mechanical connector designed:
to permit separation and removal of the replaceable endoscope tip for disposal and replacement with another replaceable endoscope tip; and
to permit connection, the separation joint designed when connected to provide mechanical force transfer applied by the surgeon's hand to the replaceable endoscope tip, the separation joint having features to transfer roll torques, the separation joint having locking features and force-transmittal surfaces at its periphery to transmit insertion and withdrawal forces across the separation joint, the separation joint's locking features and peripheral force-transmittal surfaces designed to provide stiffness in bending across the separation joint to transfer pitch and yaw torques across the separation joint, and
an electrical connector designed to provide separable electrical connectivity between electronics in the handle and the illumination emitter and imaging sensor, the handle electronics designed for drive of the illumination emitter and to receive an imaging signal from the imaging circuitry, the handle being designed to permit sterilization between uses.

24. The endoscope of claim 12, further comprising a solid and rigid sheath surrounding the bendable distal portion, the bendable distal portion being extendable from and retractable into the solid sheath under control of the surgeon via a control at the handle.

25. The endoscope of claim 12, wherein: the imaging circuitry is mounted within at or near a distal tip of the bendable distal portion via a pannable mounting.

26. The endoscope of claim 12, wherein: the plurality includes at least four segments.

27. The endoscope of claim 12, further comprising:
a flexible sheath or cover over the articulated rigid segments designed to reduce intrusion or pinching.

28. The endoscope of claim 12, wherein:
the finger engagement surface lies at a periphery of a unilateral lobe of a lever arranged to transfer push and pull forces from the surgeon's hand to direct the direction of the imaging circuitry.

29. The endoscope of claim 12, wherein:
the finger engagement surface lies at opposite portions of a periphery of a two-lobed lever arranged to transfer forces from the surgeon's hand to direct the direction of the imaging circuitry.

30. The endoscope of claim 12, wherein the finger engagement surface lies on a circular lever arranged to transfer forces from the surgeon's hand to direct two dimensions of direction of the imaging circuitry.

* * * * *